US009941089B2

(12) United States Patent
Williams et al.

(10) Patent No.: US 9,941,089 B2
(45) Date of Patent: Apr. 10, 2018

(54) CESIUM PRIMARY ION SOURCE FOR SECONDARY ION MASS SPECTROMETER

(71) Applicant: Arizona Board of Regents, a body corporate of the State of Arizona, acting for and on behalf of Arizona State University, Scottsdale, AZ (US)

(72) Inventors: Peter Williams, Phoenix, AZ (US); Karen Amanda Williams, Phoenix, AZ (US); Maitrayee Bose, Tempe, AZ (US); John Prince, Tempe, AZ (US)

(73) Assignee: ARIZONA BOARD OF REGENTS, A BODY CORPORATE OF THE STATE OF ARIZONA, ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/517,917

(22) PCT Filed: Oct. 13, 2015

(86) PCT No.: PCT/US2015/055261
§ 371 (c)(1),
(2) Date: Apr. 7, 2017

(87) PCT Pub. No.: WO2016/061057
PCT Pub. Date: Apr. 21, 2016

(65) Prior Publication Data
US 2017/0309433 A1    Oct. 26, 2017

Related U.S. Application Data

(60) Provisional application No. 62/063,023, filed on Oct. 13, 2014.

(51) Int. Cl.
*H01J 27/02* (2006.01)
*H03L 7/26* (2006.01)
(Continued)

(52) U.S. Cl.
CPC ............ *H01J 27/022* (2013.01); *H01J 49/26* (2013.01); *H01H 3/02* (2013.01); *H03L 7/26* (2013.01)

(58) Field of Classification Search
CPC ............ H03L 7/26; H01H 3/02; H01J 27/022
See application file for complete search history.

(56) References Cited

U.S. PATENT DOCUMENTS 3,967,115 A   6/1976  Kern
4,617,203 A  10/1986  Jergenson
(Continued)

OTHER PUBLICATIONS

Liebl, H., et al., "Cs+ ion microsource," Review of Scientific Instruments, vol. 59, Issue 10, Oct. 1988, American Institute of Physics, pp. 2174-2176.
(Continued)

*Primary Examiner* — Jason McCormack
*Assistant Examiner* — Sean Luck
(74) *Attorney, Agent, or Firm* — Withrow & Terranova, P.L.L.C.; Vincent K. Gustafson

(57) ABSTRACT

A primary ion source subassembly for use with a secondary ion mass spectrometer may include a unitary graphite ionizer tube and reservoir base. A primary ion source may include a capillary insert defining an ionizer aperture. An ionizer aperture may be centrally arranged in an outwardly protruding conical or frustoconical surface, and may be overlaid with a refractory metal coating or sheath. Parameters including ionizer surface shape, ionizer materials, ionizer temperature, and beam stop plate orifice geometry may be manipulated to eliminate ghost images. A graphite
(Continued)

tube gasket with a dual tapered surface may promote sealing of a source material cavity.

21 Claims, 18 Drawing Sheets

(51) Int. Cl.
    *H01H 3/02*     (2006.01)
    *H01J 49/26*     (2006.01)

(56) References Cited

U.S. PATENT DOCUMENTS

| | | | |
|---|---|---|---|
| 5,144,143 A * | 9/1992 | Raspagliesi | H01J 27/08 |
| | | | 250/426 |
| 5,936,251 A | 8/1999 | Gierak et al. | |
| 2009/0200485 A1 | 8/2009 | Kolodney et al. | |

OTHER PUBLICATIONS

International Preliminary Report on Patentability for PCT/US2015/055261, dated Apr. 27, 2017, 6 pages.
International Search Report and Written Opinion for PCT/US2015/055261, dated Feb. 9, 2016, 11 pages.

\* cited by examiner

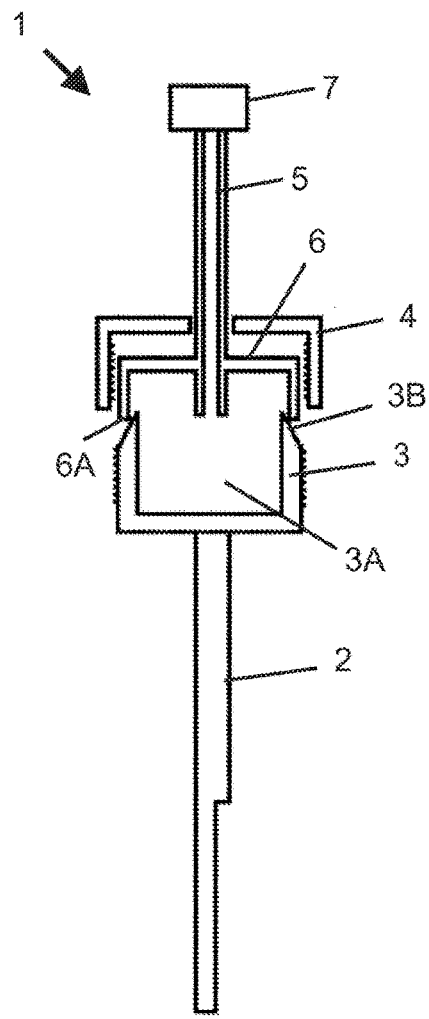
FIG._1A
(RELATED ART)
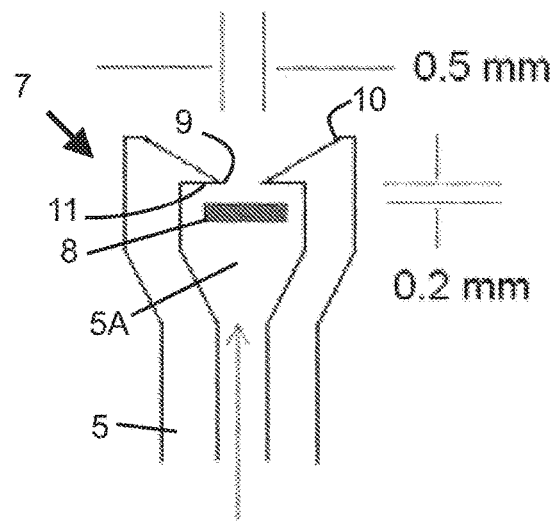
$Cs_2CO_3$ vapor
FIG._1B
(RELATED ART)

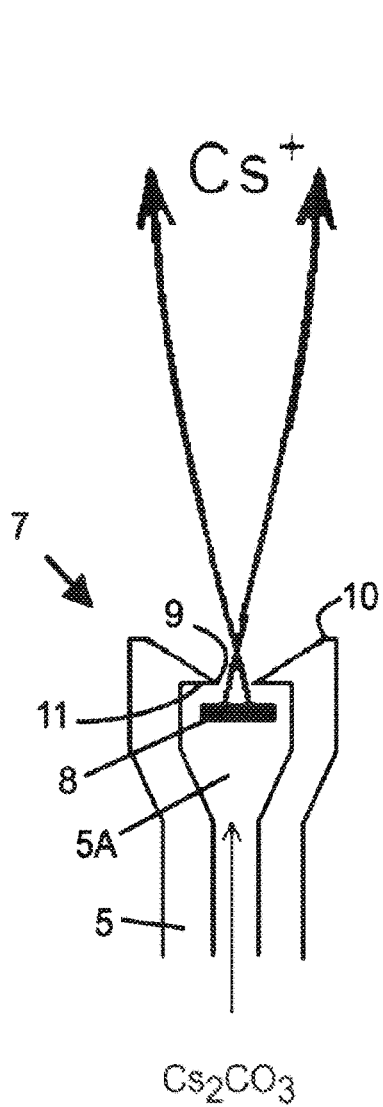
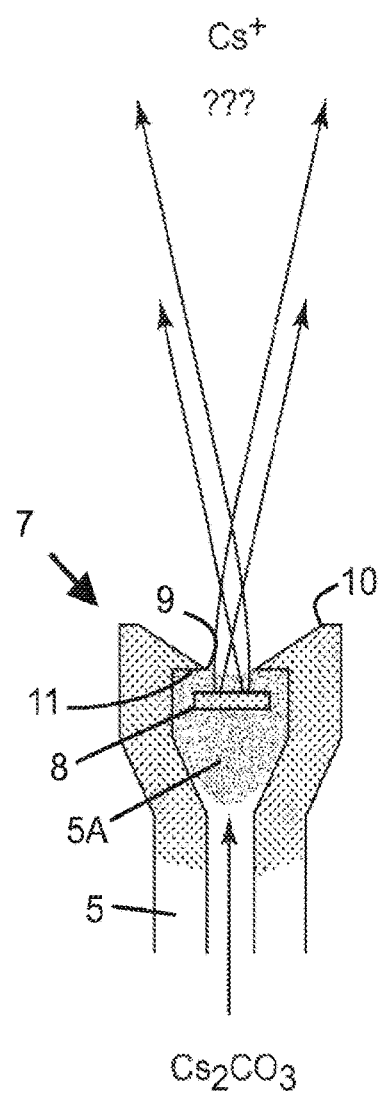
FIG._1C
(RELATED ART)
FIG._1D
(RELATED ART)

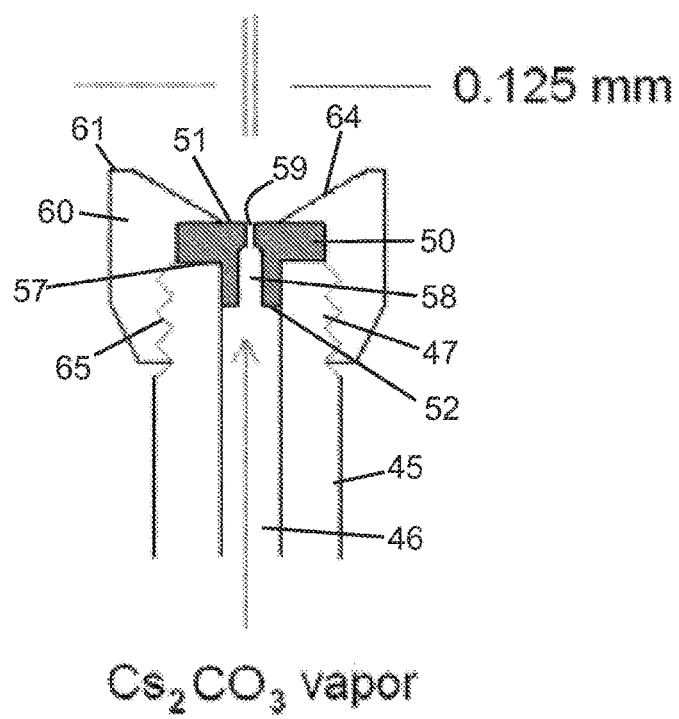
$Cs_2CO_3$ vapor
FIG._3A
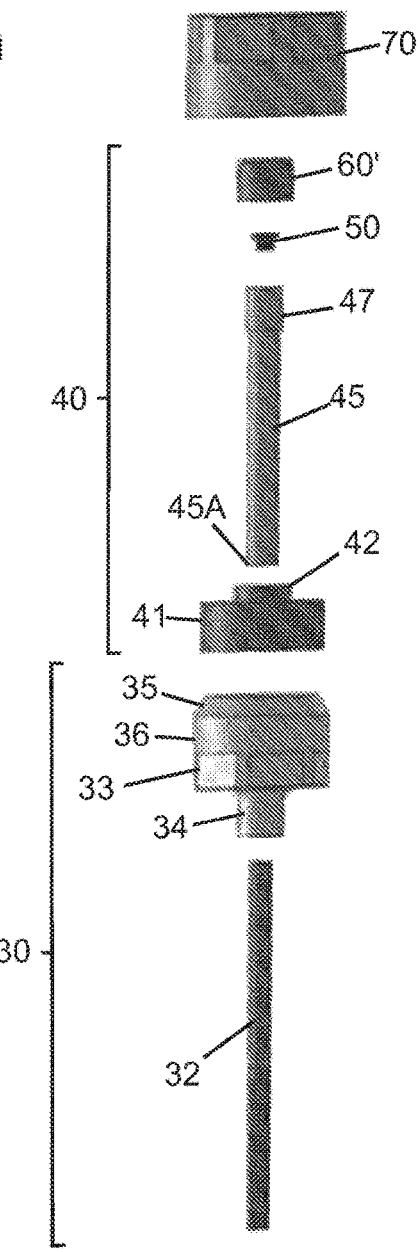
FIG._3B

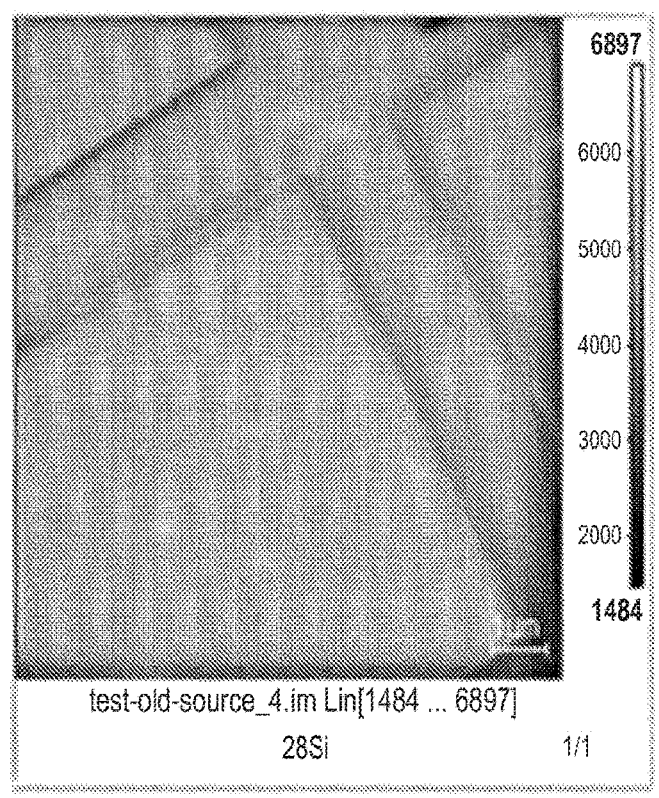
FIG._4A
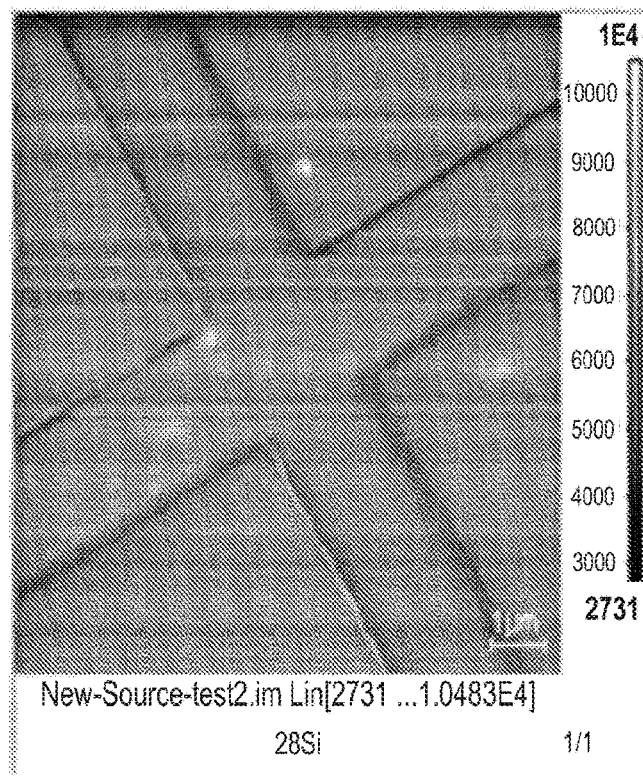
FIG._4B

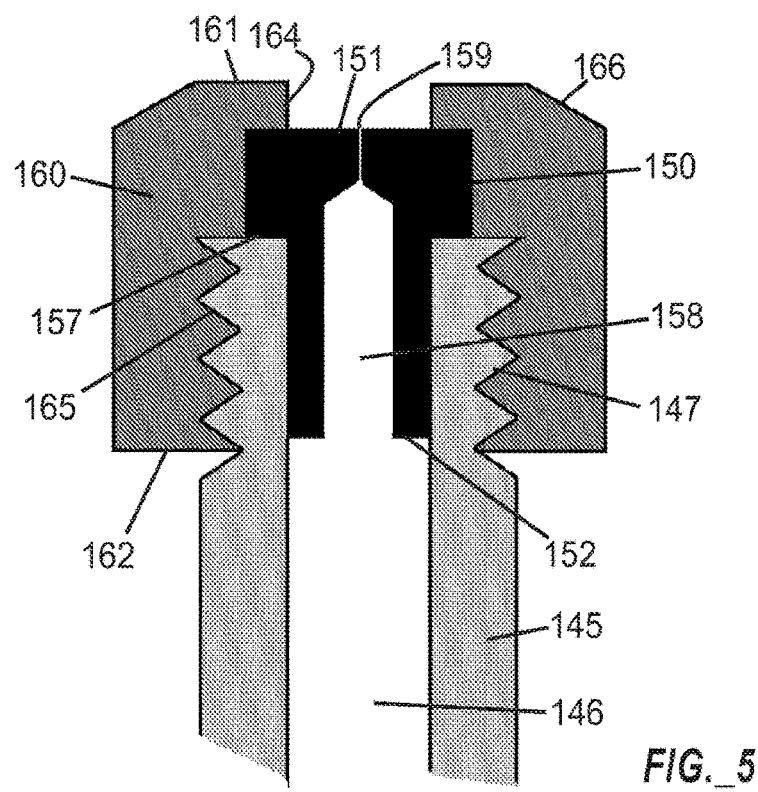
FIG._5
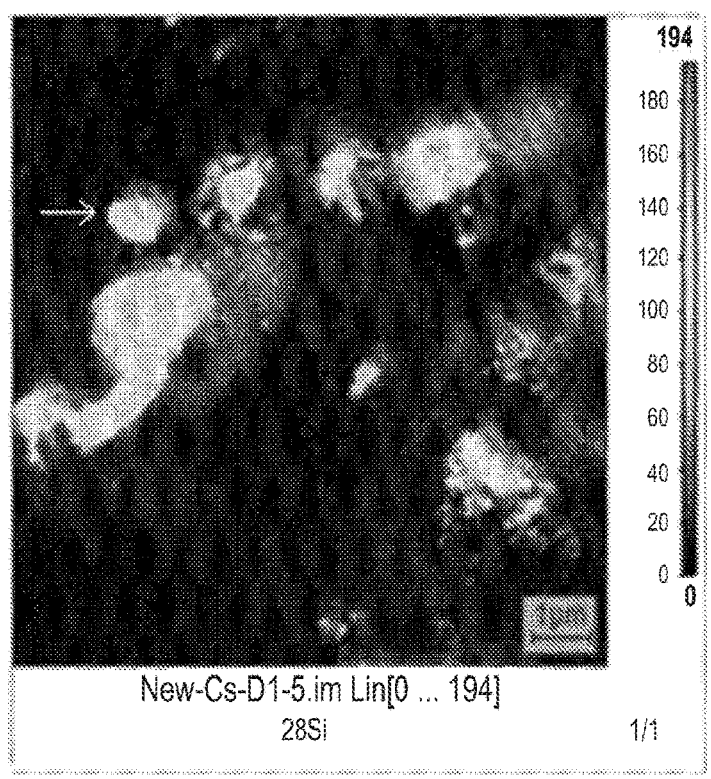
FIG._6

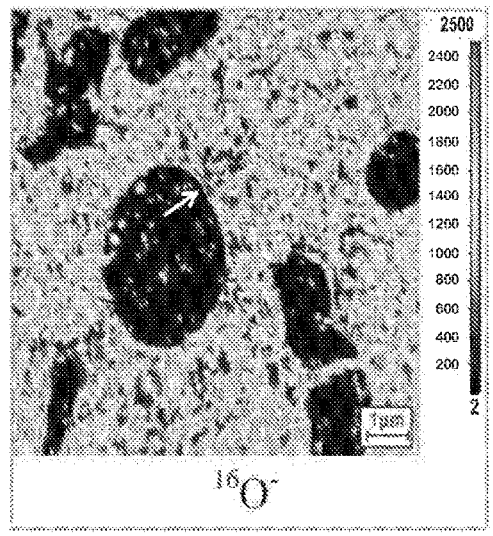
FIG._8A
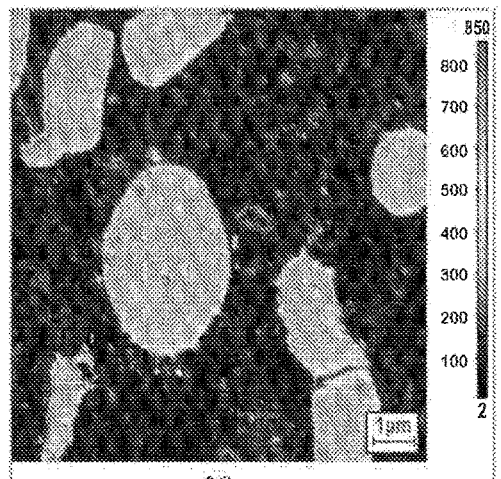
FIG._8B
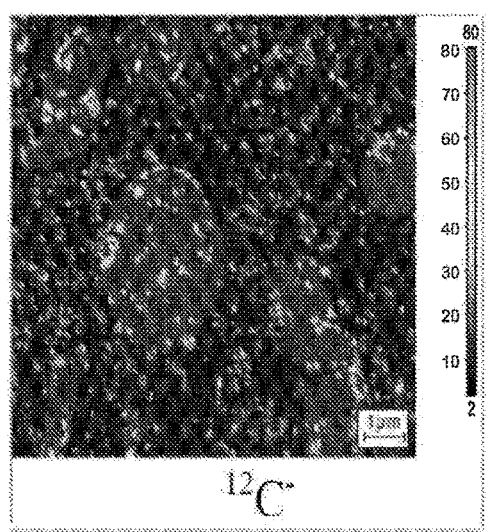
FIG._8C

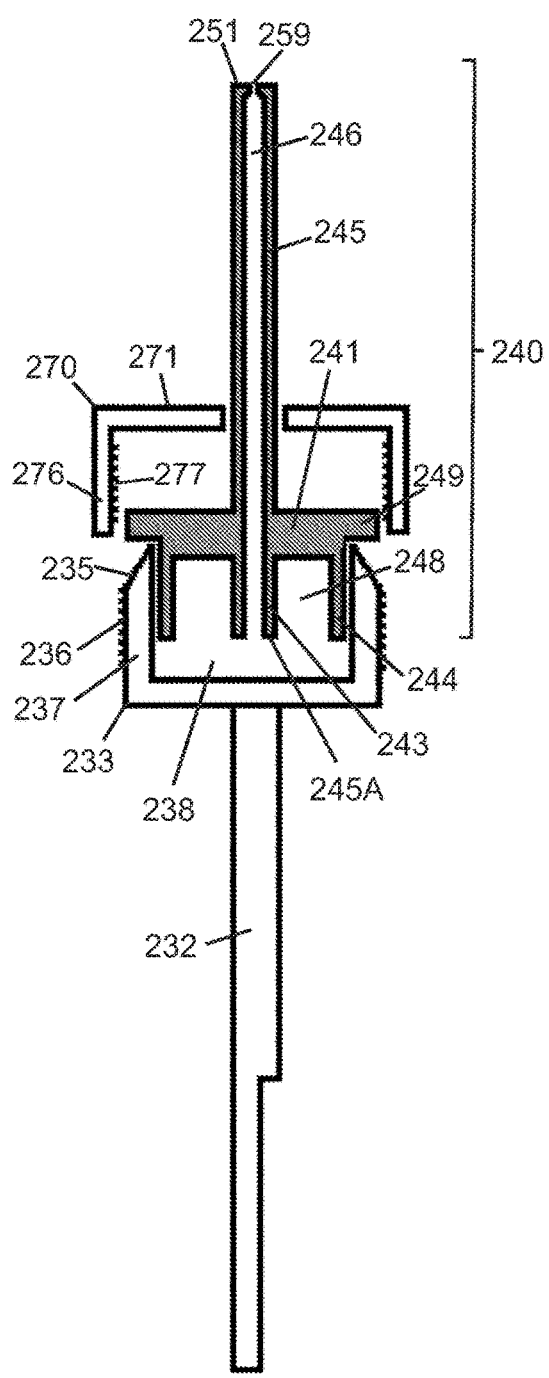
FIG._11
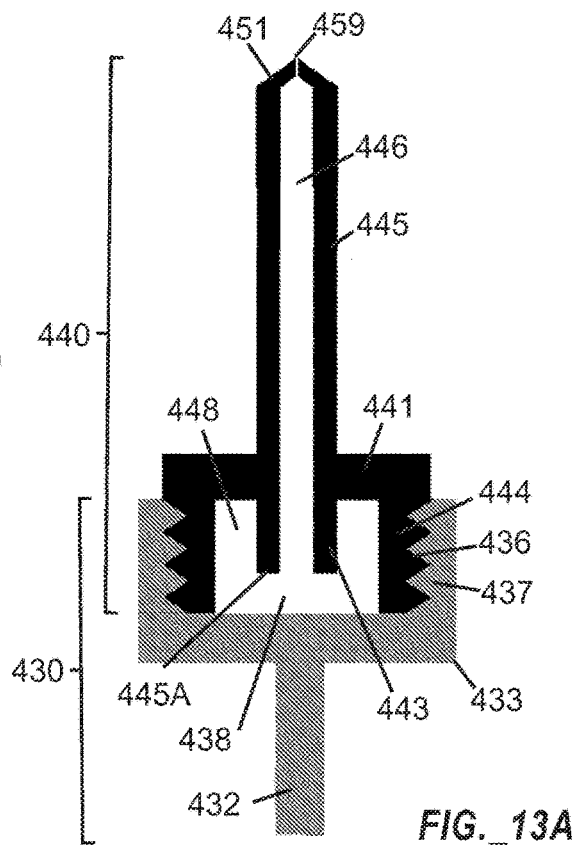
FIG._13A
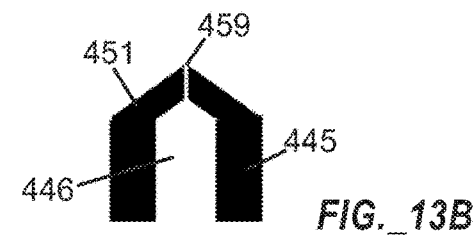
FIG._13B
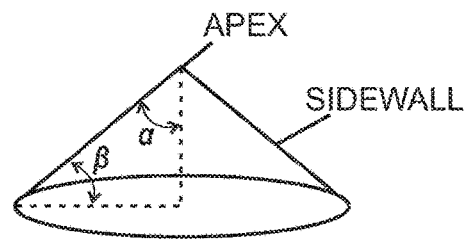
FIG._14

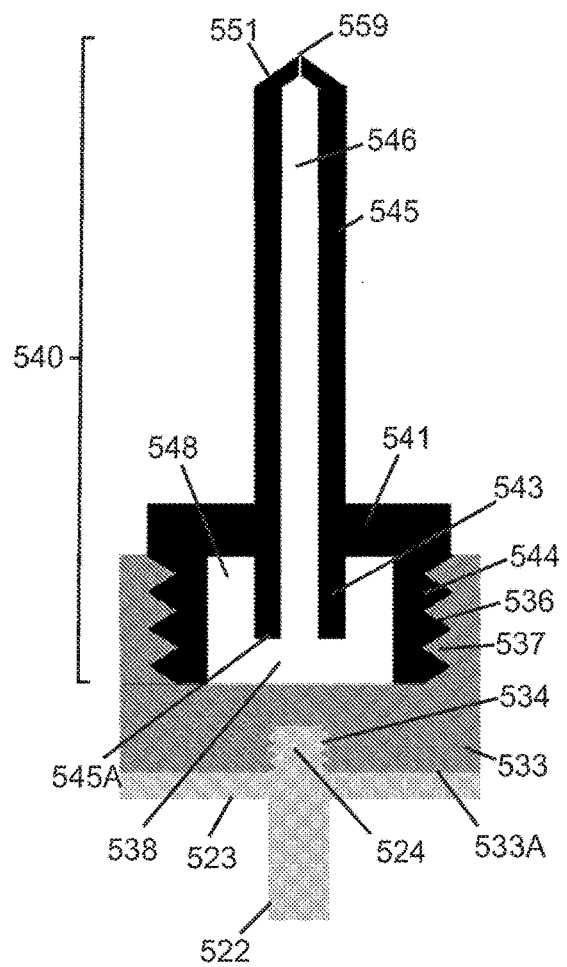
FIG._15
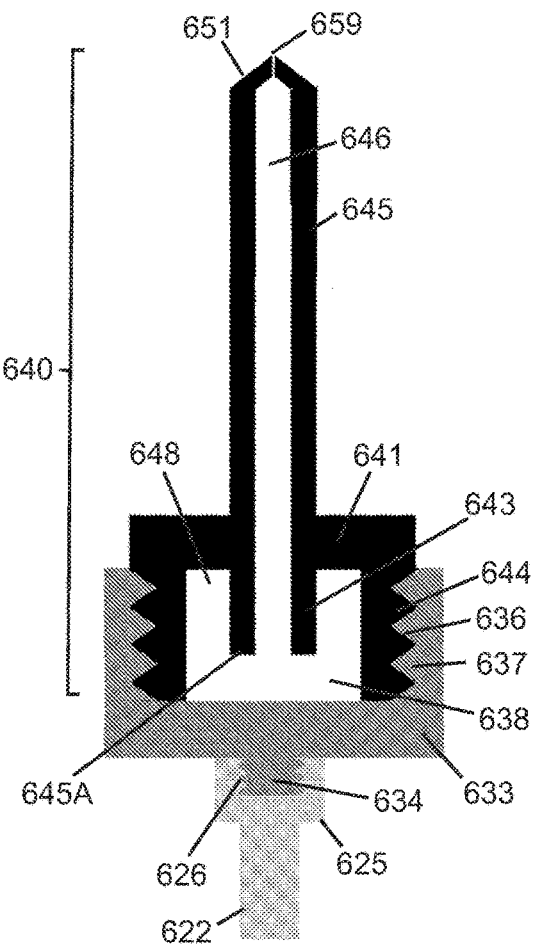
FIG._16

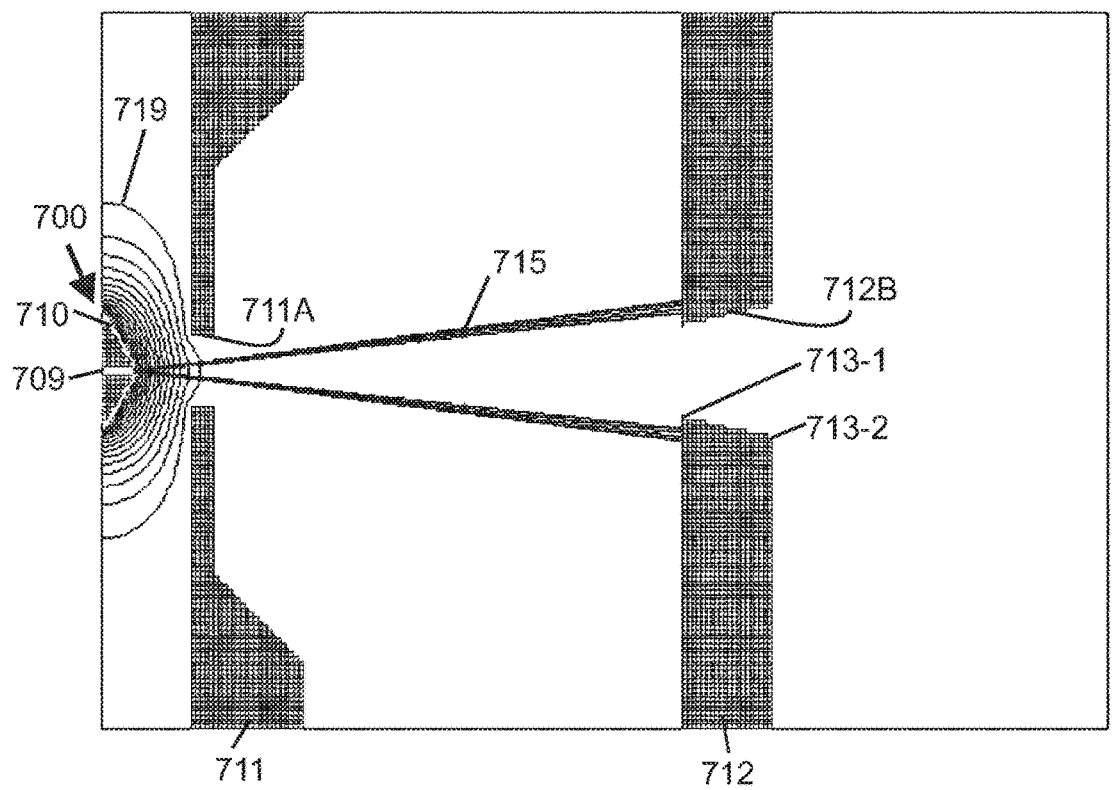
FIG._18A
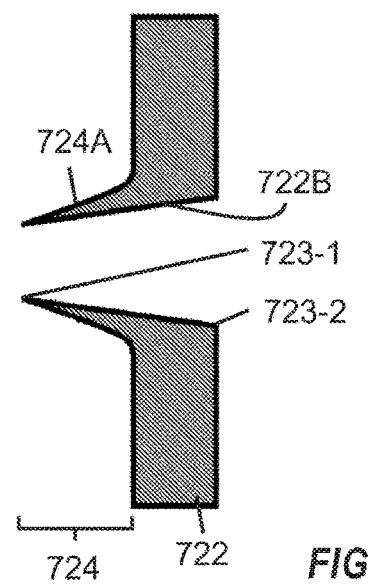
FIG._18B

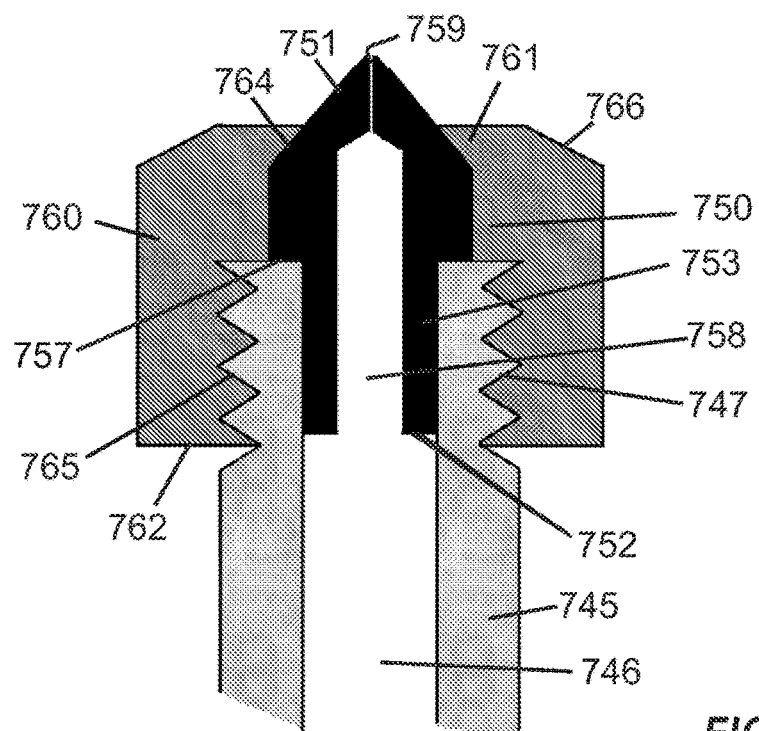
FIG._19
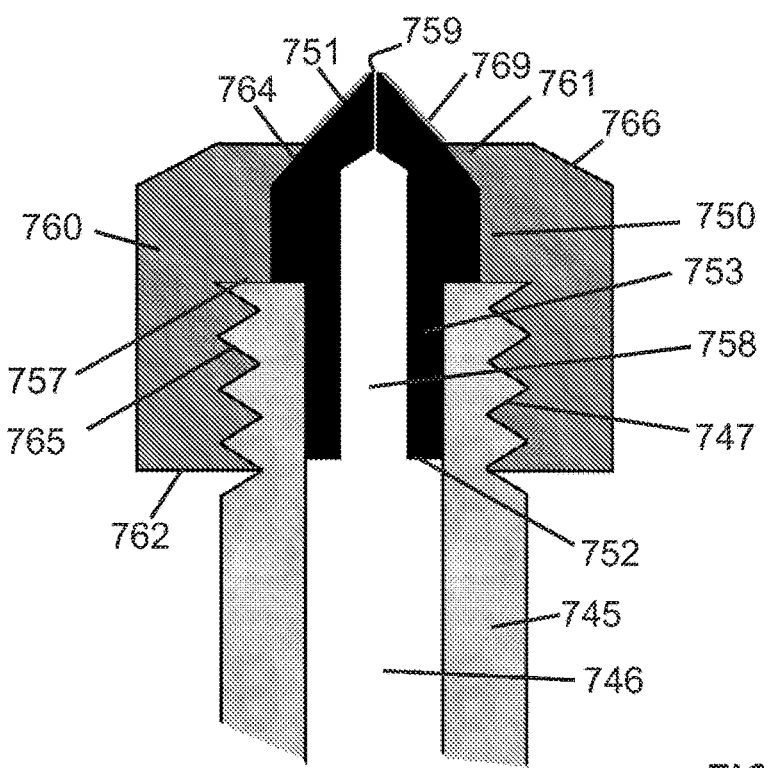
FIG._22

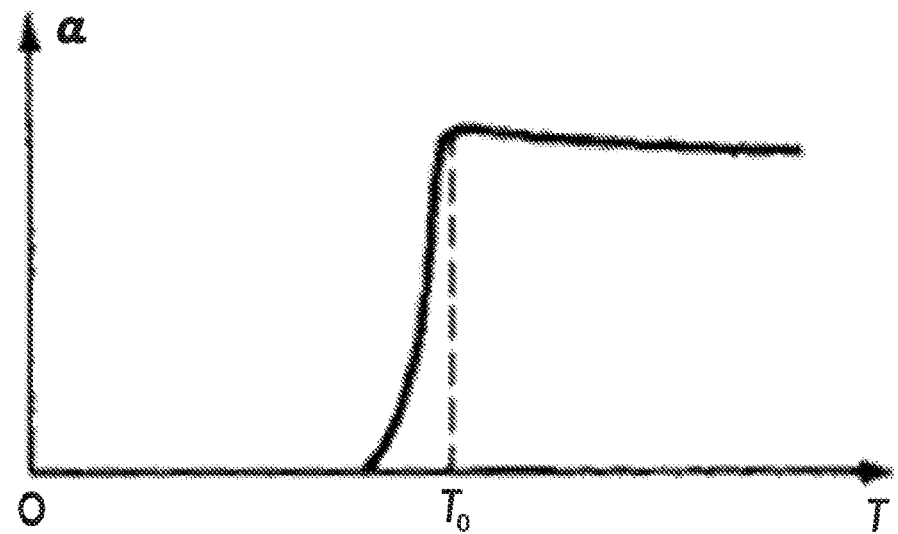
FIG._20
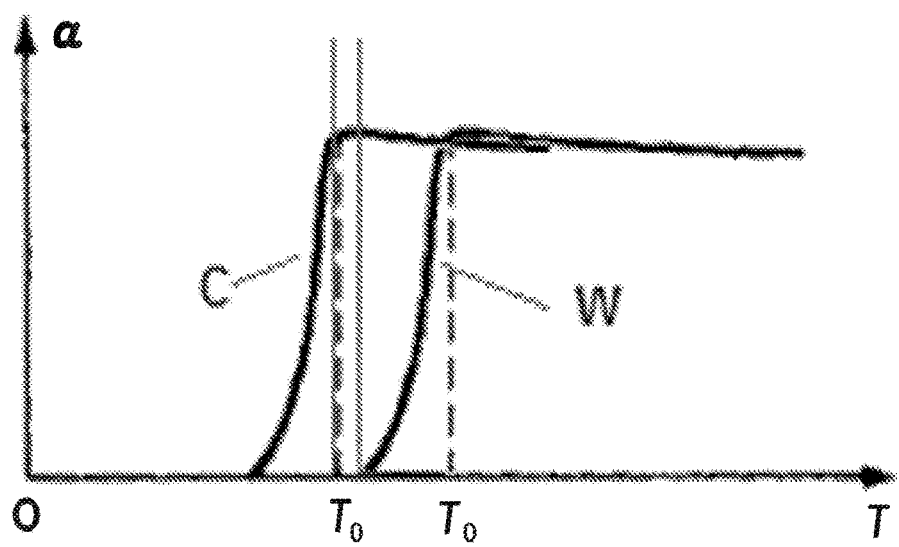
FIG._21

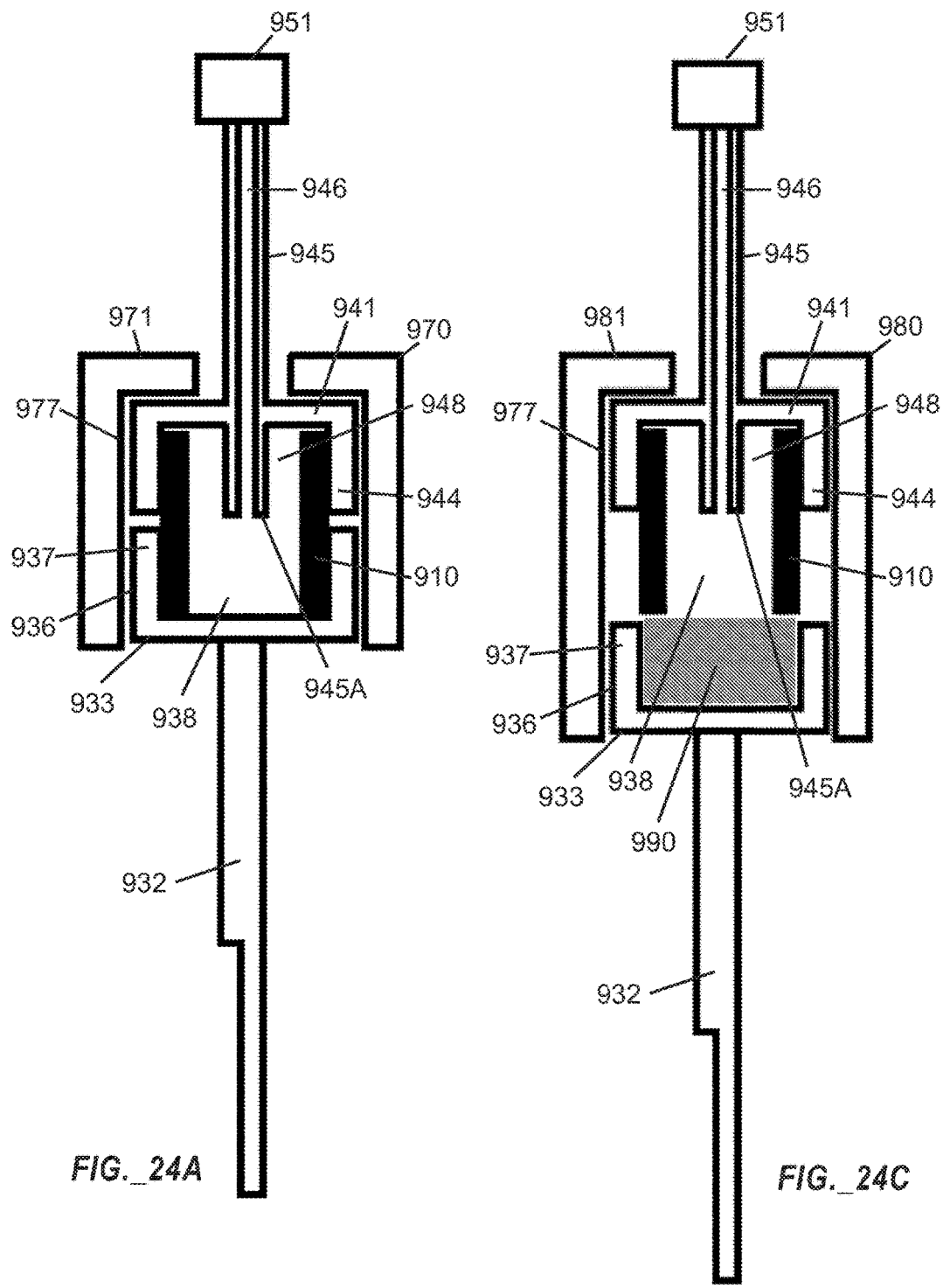
FIG._24A
FIG._24C

CESIUM PRIMARY ION SOURCE FOR SECONDARY ION MASS SPECTROMETER

CROSS-REFERENCE TO RELATED APPLICATION(S)

This application is a 35 U.S.C. § 371 national phase filing of International Application No. PCT/US2015/055261 filed on Oct. 13, 2015, and claims the benefit of U.S. Provisional Patent Application No. 62/063,023 filed on Oct. 13, 2014. The contents of the foregoing applications are hereby incorporated by reference herein.

TECHNICAL FIELD

This disclosure concerns primary ion sources for secondary ion mass spectrometers, and methods for fabricating such ion sources.

BACKGROUND

Secondary ion mass spectrometry (SIMS) is a widely-used surface and thin film analytical technique that finds wide application in the semiconductor industry, in geochemistry and materials research, and other technical areas. Over 500 commercial instruments exist world-wide. The technique generates an analytical signal by bombarding a sample with an energetic ion beam (the "primary" ion beam) that "sputters" atoms from the sample surface. Each impact of a 5-15 keV primary ion ejects a small number of atoms from the target surface. A fraction of the ejected atoms are ionized upon ejection and these "secondary" ions can be accelerated into a mass spectrometer and mass-analyzed to yield information about the chemical and isotopic make-up of the sample.

The efficiency of secondary ion formation can be increased by using chemically active primary ion species which are implanted in the target surface and alter its surface chemistry: electronegative primary ion species such as oxygen are used to enhance positive secondary ion yields, and electropositive primary ion species such as cesium ions are used to enhance negative ion yields (i.e., secondary negative ions of electronegative species).

The SIMS technique provides a unique combination of extremely high sensitivity for almost all elements from hydrogen to uranium and above (e.g., detection limit down to ppb level for many elements), high lateral resolution imaging (e.g., down to 50 nm currently), and a very low background that allows high dynamic range (e.g., more than 5 decades). This technique is "destructive" by its nature, since it involves sputtering of material to generate an ion signal. It can be applied to any type of material (insulators, semiconductors, metals) that can stay under vacuum.

One major strength of the SIMS technique is that it embodies a microanalytical method. The primary ion beam can be focused to a tiny spot so that chemical analysis can be performed on extremely tiny areas; alternatively, by rastering the focused beam over a sample surface while monitoring ion signals, chemical and isotopic images of the sample surface can be produced with excellent spatial resolution.

At present, the epitome of imaging performance occurs in an instrument called NanoSIMS (manufactured by Cameca, Paris, France), which has a present cost of approximately $4 million. This instrument has precisely designed primary ion optics intended to focus the primary ion beams to the smallest possible spot on the sample surface. The specified minimum beam size with the factory ion source is 50 nm, typically obtained with a beam current at the sample of ~0.25 picoamps (pA).

The factory ion source design of a NanoSIMS instrument is schematically illustrated in FIG. 1A. The source 1 is fabricated completely of metal—mainly molybdenum, but with part of the ionizer section 7 being tungsten. The source 1 includes a mounting post 2, a heated molybdenum reservoir body 3 supported by the mounting post 2 and including a reservoir cavity 3A arranged to hold a cesium salt (e.g., cesium carbonate), a molybdenum narrow tube assembly 5 (including a wide base portion 6 serving as a portion of the reservoir), and a strongly-heated ionizer section 7 arranged to receive cesium carbonate vapor from the reservoir via the narrow tube. The narrow tube assembly 5 feeds cesium carbonate vapor from the heated reservoir body 3 to the strongly-heated ionizer section 7 and also provides a degree of thermal isolation between the reservoir body 3 and the ionizer section 7. An outer edge portion of the reservoir body 3 includes a beveled surface 3B. A bounding surface 6A of the wide base portion 6 of the narrow tube assembly 5 is arranged to abut the beveled surface 3B of the reservoir body 3. The reservoir body 3 is externally threaded and is arranged to receive an internally threaded sealing cap screw 4 that fits around the wide base portion 6 to form a swage-type seal. Sealing between the molybdenum wide base portion 6 and the molybdenum reservoir body 3 is a crucial issue for this ion source 1, since leakage causes poor performance of the electron impact heating system and ultimately causes noisy images. The swage-type seal between the two molybdenum reservoir portions 3, 6 utilized with the factory ion source 1 requires close control of the sealing force and is not designed to be demountable, so the ion source 1 cannot be reused.

A detailed view of the ionizer section of a NanoSIMS factory source is shown in FIG. 1B. A tip 10 of the ionizer section 7 serves as an electrode and defines an outlet aperture 9. A flat tungsten ionizer plate 8 is arranged in a widened cavity 5A between the narrow tube 5 (at bottom) and the outlet aperture 9. The aperture 9 typically has a diameter of about 0.5 mm (500 μm), and the tungsten ionizer plate 8 is typically spaced a distance of about 0.2 mm (200 μm) apart from an internal surface 11 of the tip 10 that serves as an electrode and that defines the aperture 9.

The intended (or design objective) operation of the ionizer section 7 is shown in FIG. 10, with further reference to structures depicted in FIG. 1A arranged upstream of the ionizer section 7. The reservoir body 3 is heated to cause cesium carbonate vapor to diffuse up the narrow tube 5 and decompose as the vapor reaches the strongly-heated ionizer section 7 (e.g., which is heated to about 1200° C.) where the vapor flows onto the flat tungsten ionizer plate 8. The ionizer section 7 is strongly heated (e.g., by a combination of electron bombardment and radiative heating from the electron emitting filament) and cesium atoms that impact the tungsten ionizer plate 8 evaporate almost 100% as positive ions. The source is held at high potential (+8 kV in the NanoSIMS) very close to a grounded extraction plate (not shown) and the cesium ions are extracted by the high electric field penetrating through the 500 μm aperture 9 in the electrode tip 10 around the ionizer plate 8. As shown in FIG. 10, this shaped electric field is designed to electrostatically accelerate ions and draw the ions into a small "crossover" that forms the ion-optical "object" for the focusing optics of the primary ion column to focus to a demagnified image at the sample (such as the 50 nm diameter factory specification for the NanoSIMS).

In practice, actual operation of the ionizer section differs from the intended operation schematically illustrated in FIG. 10. FIG. 1D illustrates the practical operation of the foregoing ionizer section 7. In practice, it is impossible to heat only the ionizer plate 8; instead, the entire ionizer head is heated and cesium ions are formed on (and extracted from) all surfaces throughout the ionizer volume. Arguably, cesium ions can be formed in, and extracted from a region 500 μm in diameter and 200 μm deep. This makes for a more diffuse ion-optical object, and this in turn results in the focused image at the sample being limited to the factory specification of 50 nm diameter. Compared to the design objective schematically illustrated in FIG. 1C, in practical operation the initial ion beam crossover is significantly compromised.

The factory ion source 1 shown in FIG. 1A is typically replaced one to several times per year (e.g., upon exhaustion of cesium salt source material), with the frequency of replacement depending on use of a NanoSIMS instrument. Such "disposable" ion sources cost about $3000 for each replacement.

An alternative ionizer design was developed at Arizona State University for use with an early version Cameca SIMS instrument ims 3f (i.e., not the NanoSIMS instrument) around the year 2000. In one version, a ⅛" outside diameter, 1/16" inside diameter alumina tube, approximately 3" long is used. One end of the tube is sealed with a commercial alumina cement plug and a fine hole or orifice (e.g., 0.010" or 250 μm in diameter) is drilled through the cement plug. A quantity (approximately 0.15 g) of cesium carbonate is loaded into the other end of the tube, which is sealed with an alumina cap cemented in place with alumina cement. The end of the tube with the fine orifice is inserted into a resistance heater including heating elements and heated to approximately 1200° C. The $Cs_2CO_3$ charge is heated by heat conduction along the tube and vaporizes either as $Cs_2CO_3$ or after decomposition to $Cs_2O$; the resulting vapor then effuses out of the orifice. At the high temperature in the orifice, the vapor dissociates to atomic cesium. Almost every cesium atom traversing the orifice makes multiple collisions with the heated alumina surface and has a very high probability of being thermally surface-ionized. The orifice ionizer produces a high flux density of cesium atoms through a tiny central area which can be accurately aligned with the primary ion column of the secondary ion mass spectrometer. Moreover, as compared to conventional ionizers fabricated out of expensive tungsten metal, the use of alumina (in particular alumina cement) means that the heat-resistant ionizer portion of the source is very inexpensive to fabricate because the alumina cement can be very easily drilled before heat-setting, or the cement plug can be formed around a fine wire insert which is later removed after the cement has set. The early version Cameca SIMS instrument with the ionizer section outlined above did not have a primary ion column capable of focusing the ion beam to an extremely fine spot; however, it was demonstrated that the total ion current was competitive with other ion sources of the era.

A graphite-based variant of the above-described alumina-based orifice ionizer section was developed at Arizona State University and has been in use at such institution since about 2001. The design of the graphite-based ionizer section 17 is shown in FIG. 2. Such ionizer section 17 includes a channel or orifice 29 fabricated in a graphite plug 20 that is screwed into a molybdenum reservoir tube 15 via threads 23 proximate to an end 15' of the tube 15, with the tube 15 and plug 20 being heated by a resistance heater 12 including heating elements 13 arranged external to the molybdenum tube 15 and graphite plug 20. The molybdenum tube 15 is internally threaded and is arranged to receive external threads of the graphite plug 20. As shown in FIG. 2, the channel or orifice 29 has a diameter of 0.125 mm (125 μm), and the end surface 21 of the plug 20 is substantially flush with an end surface 28 of the reservoir tube 15.

Use of graphite confers certain benefits. Graphite is highly refractory so that it withstands the high temperature needed for surface ionization. Yet unlike refractory metals, graphite is soft and amenable to drilling with a fragile 0.005" (125 micron) diameter drill. The softness of graphite also allows facile sealing of the drilled graphite insert to the metal reservoir tube. In FIG. 2, a beveled base 22 of the graphite plug 20 is forced into a sharp metal edge 16 of the tube 15, thereby cutting into the graphite material of the graphite plug 20 and providing a vapor seal. The surface work function of graphite is ~4.5 electron-volts, comparable to tungsten and higher than the ionization potential of cesium (3.9 electron-volts), which ensures almost 100% ionization efficiency for cesium on the heated graphite surface.

The art continues to seek cesium ion sources for use with SIMS instruments that are capable of providing improved performance and reduced cost. Aspects of this disclosure address shortcomings associated with conventional systems and methods.

SUMMARY

Aspects of this disclosure relate to a primary ion source, and a primary ion source subassembly, arranged for use with a secondary ion mass spectrometer.

In certain aspects, the disclosure relates to a primary ion source subassembly arranged for use with a secondary ion mass spectrometer, the primary ion source subassembly comprising an ionizer tube and reservoir base, wherein the ionizer tube and the reservoir base are unitary and formed of a continuous graphite or graphite-containing body material. In certain embodiments, a portion of the reservoir base is configured to bound and/or be received in a cylindrical cavity of a cavity-defining reservoir body. In certain embodiments, the reservoir base and a first portion of the ionizer tube in combination define an annular recess that is arranged to be exposed to and/or received in the cylindrical cavity of the cavity-defining reservoir body, and a second portion of the ionizer tube extends outwardly from the reservoir base. In certain embodiments, the second portion of the ionizer tube comprises a distal end defining an ionizer aperture having a reduced diameter in comparison to a nominal or average diameter of a passage within the ionizer tube. In certain embodiments, the distal end of the ionizer tube comprises an outwardly protruding conical or frustoconical surface, and the ionizer aperture extends through a central axis of the conical or frustoconical surface. In certain embodiments, the conical or frustoconical surface comprises a complementary conical half-angle in a range of from 6 to 45 degrees. In certain embodiments, a refractory metal coating or refractory metal sheath is arranged over at least a portion of the conical or frustoconical surface. In certain embodiments, the ionizer aperture comprises a diameter of no greater than about 125 μm, or a diameter no greater than 50 μm, and may be defined by mechanical drilling or laser drilling. In certain embodiments, the reservoir base comprises a radially extending lip arranged to be compressibly received between (i) an outer edge portion of the cavity-defining reservoir body and (ii) a sealing cap arranged to threadedly engage a portion of the cavity-defining reservoir body. In certain embodiments, the reservoir base comprises a tapered graphite cylinder with an outer diameter that varies with position from a maximum diameter value greater than the inner diameter of the cavity-defining reservoir body at the end closest to the ionizer to a reduced diameter value smaller than the inner diameter of the cavity-defining reservoir body at the end furthest from the ionizer, and a sealing cap arranged to threadedly engage a portion of the cavity-defining reservoir body and to force the tapered graphite cylinder into the cavity-defining reservoir body. In certain embodiments, a portion of the reservoir base comprises an externally threaded surface that is arranged to mate with an internally threaded surface of the cavity-defining reservoir body. In certain embodiments, a graphite powder or graphite coating is arranged between the externally threaded surface and the internally threaded surface. In certain embodiments, a primary ion source is arranged for use with a secondary ion mass spectrometer, the primary ion source comprising: a reservoir body comprising a cylindrical cavity; and the primary ion source subassembly, wherein a portion of the reservoir base is received in the cylindrical cavity. In certain embodiments, the reservoir body comprises graphite. In certain embodiments, the primary ion source further comprises a sealing cap arranged to threadedly engage a portion of the reservoir body, and arranged to sealingly engage the primary ion source subassembly to the reservoir body.

In certain aspects, the disclosure relates to a primary ion source arranged for use with a secondary ion mass spectrometer, the primary ion source comprising: a tube configured to receive cesium-containing vapor from a reservoir, wherein the tube includes an externally threaded surface, includes an internal passage, and includes a first end; a capillary insert including a body defining an ionizer aperture, wherein at least a portion of the capillary insert is configured to be received by the internal passage along the first end, with the ionizer aperture arranged to receive cesium-containing vapor from the internal passage; and a cap defining an orifice, including a cavity arranged to receive a portion of the capillary insert with the orifice registered with the ionizer aperture, and including an internally threaded surface arranged to engage the externally threaded surface of the tube to cause sealing engagement between the capillary insert and the tube. In certain embodiments, the body of the capillary insert comprises a distal end arranged to extend through the orifice defined in the cap, the distal end comprises an outwardly protruding conical or frustoconical surface, and the ionizer aperture extends through a central axis of the conical or frustoconical surface. In certain embodiments, the conical or frustoconical surface comprises a complementary conical half-angle in a range of from 6 to 45 degrees. In certain embodiments, the body of the capillary insert comprises graphite or graphite-containing material, and the capillary insert further comprises a refractory metal coating or sheath arranged over at least a portion of the conical or frustoconical surface. In certain embodiments, the capillary insert comprises a material having a lower hardness than each of (i) a material of fabrication of the tube and (ii) a material of fabrication of the cap. In certain embodiments, the capillary insert is fabricated of graphite material. In certain embodiments, a first portion of the capillary insert comprises a first width and is configured to be received by the internal passage along the first end, and a second portion of the capillary insert comprises a second width and is configured to be arranged outside the internal passage, wherein the second width is greater than the first width. In certain embodiments, at least one of the tube and the cap comprises molybdenum. In certain embodiments, a graphite powder or graphite coating is arranged between the externally threaded surface and the internally threaded surface. In certain embodiments, the ionizer aperture comprises a diameter of no greater than about 125 μm, or a diameter no greater than 50 μm, and may be defined by mechanical drilling or laser drilling.

In certain aspects, the disclosure relates to a primary ion source arranged for use with a secondary ion mass spectrometer, the primary ion source comprising: a reservoir base; a reservoir body comprising an externally threaded surface; a tubular gasket arranged between the reservoir base and the reservoir body, wherein the tubular gasket comprises graphite or a graphite-containing body material, the tubular gasket comprises a first end and a second end, and the tubular gasket comprises an outer diameter that varies with position from a maximum diameter value at an intermediate point to reduced diameter values at the first end and the second end; an ionizer tube arranged in fluid communication with a reservoir cavity bounded by a portion of the reservoir base, a portion of the reservoir body, and the tubular gasket; and a sealing nut comprising internal threads arranged to engage the externally threaded surface. In certain embodiments, at least one of the reservoir base and the reservoir body comprises a metal. In certain embodiments, at least one of the reservoir base and the reservoir body comprises graphite or a graphite-containing material. In certain embodiments, the ionizer tube and the reservoir base are unitary and formed of a continuous graphite or graphite-containing body material. In certain embodiments, the ionizer tube comprises a proximal end proximate to the reservoir body, and the ionizer tube comprises a distal end defining an ionizer aperture having a reduced diameter in comparison to a nominal or average diameter of a passage within the ionizer tube. In certain embodiments, the distal end of the ionizer tube comprises an outwardly protruding conical or frustoconical surface, and the ionizer aperture extends through a central axis of the conical or frustoconical surface. In certain embodiments, the primary ion source further comprises a refractory metal coating or refractory metal sheath arranged over at least a portion of the conical or frustoconical surface. In certain embodiments, the primary ion source further comprises a capillary insert including a body defining an ionizer aperture, wherein at least a portion of the capillary insert is configured to be received by the ionizer tube; and a cap defining an orifice, including a cavity arranged to receive a portion of the capillary insert with the orifice registered with the ionizer aperture, and including an internally threaded surface arranged to engage an externally threaded surface of the ionizer tube to cause sealing engagement between the capillary insert and the ionizer tube. In certain embodiments, the capillary insert comprises graphite or a graphite-containing material. In certain embodiments, the body of the capillary insert comprises a distal end arranged to extend through the orifice defined in the cap, the distal end comprises an outwardly protruding conical or frustoconical surface, and the ionizer aperture extends through a central axis of the conical or frustoconical surface. In certain embodiments, the body of the capillary insert comprises graphite or graphite-containing material, and the capillary insert further comprises a refractory metal coating or sheath arranged over at least a portion of the conical or frustoconical surface.

In another aspect, the disclosure relates to a primary ion source arranged for use with a secondary ion mass spectrometer, the primary ion source comprising: an ionizer tube configured to receive cesium-containing vapor from a reservoir, and a distal end portion comprising an outwardly protruding conical or frustoconical surface, wherein an ionizer aperture extends through a central axis of the conical or frustoconical surface, and the ionizer aperture is arranged to receive cesium-containing vapor from the ionizer tube. In certain embodiments, the distal end portion and the ionizer tube embody a continuous body structure. In certain embodiments, the primary ion source further comprises a refractory metal coating or refractory metal sheath arranged over at least a portion of the conical or frustoconical surface. In certain embodiments, the distal end portion comprises a capillary insert received by the ionizer tube, wherein the capillary insert defines the conical or frustoconical surface and defines the ionizer aperture; and the primary ion source further comprises a cap defining an orifice, the cap including a cavity arranged to receive a portion of the capillary insert with the orifice registered with the ionizer aperture, and the cap including an internally threaded surface arranged to engage an externally threaded surface of the ionizer tube to cause sealing engagement between the capillary insert and the ionizer tube. In certain embodiments, the primary ion source further comprises a refractory metal coating or refractory metal sheath arranged over at least a portion of the conical or frustoconical surface. In certain embodiments, a medial portion of the cap comprises a tapered surface overlying at least a portion of the conical or frustoconical surface, wherein the tapered surface comprises a refractory metal sheath.

In another aspect, the disclosure relates to an ion supply assembly arranged for use with a secondary ion mass spectrometer, the ion supply assembly comprising: a primary ion source as disclosed herein; an extraction plate defining an extraction plate orifice registered with the ionizer aperture; and a beam stop plate defining a beam stop plate orifice registered with the extraction plate orifice. In certain embodiments, the ion supply assembly is arranged to prevent passage through the beam stop plate orifice of cesium ions other than cesium ions emanating directly from the ionizer aperture, In certain embodiments, the following parameters are selected to prevent passage through the beam stop plate orifice of cesium ions other than cesium ions emanating directly from the ionizer aperture: (a) shape of the distal end portion, (b) materials of the distal end portion, and (c) size and shape of the beam stop plate orifice. In certain embodiments, the beam stop plate orifice comprises a reduced diameter portion proximate to the primary ion source, and comprises an increased diameter portion distal from the primary ion source. In certain embodiments, the beam stop plate orifice comprises a frustoconical cross-sectional shape. In certain embodiments, the beam stop plate comprises a frustoconical extension, and the reduced diameter portion is defined through the frustoconical extension.

In another aspect, the disclosure relates to an ion supply assembly arranged for use with a secondary ion mass spectrometer, the ion supply assembly comprising: a primary ion source arranged to discharge ions through an ionizer aperture; an extraction plate defining an extraction plate orifice registered with the ionizer aperture; and a beam stop plate defining a beam stop plate orifice registered with the extraction plate orifice, wherein the beam stop plate orifice comprises a reduced diameter proximate to the primary ion source, and comprises an increased diameter distal from the primary ion source. In certain embodiments, the beam stop plate orifice comprises a frustoconical cross-sectional shape.

In certain embodiments, an ionizer is operated at a temperature selected so that cesium ions are emitted with high efficiency from an ionizer aperture defined in a graphite element, and so that cesium ions are emitted with low efficiency from a refractory metal coating or refractory metal sheath arranged proximate to the ionizer aperture.

In certain aspects, any of the preceding aspects or other features disclosed here may be combined for additional advantage.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

FIG. 1A is a cross-sectional schematic illustration of a factory primary ion source of a NanoSIMS secondary ion mass spectrometer instrument.

FIG. 1B is a magnified cross-sectional schematic illustration of an ionizer section of the factory primary ion source of a NanoSIMS secondary ion mass spectrometer instrument.

FIG. 1D illustrates the ionizer section of FIGS. 1B-1C, illustrating trajectory of cesium ions more closely resembling actual operation.

FIG. 3A is a magnified cross-sectional schematic illustration of an ionizer section including a capillary insert defining an ionizer aperture and retained by a threaded cap according to one embodiment and intended for use with a secondary mass spectrometer instrument.

FIG. 3B is an exploded elevation view of an ion source for a secondary mass spectrometer instrument, utilizing an ionizer section similar to the design of FIG. 3A.

FIG. 4A is an image of an etched silicon test grid obtained with a NanoSIMS secondary ion mass spectrometer instrument using a factory primary ion source (i.e., according to FIG. 1B).

FIG. 4B is an image of an etched silicon test grid obtained with a NanoSIMS secondary ion mass spectrometer instrument using an ion source according to FIG. 3B.

FIG. 5 is a cross-sectional schematic illustration of an ionizer section according to another embodiment, the ionizer section including a capillary insert defining an ionizer aperture and retained by a threaded cap having a different shape than the cap of FIG. 3A.

FIG. 6 is an image using silicon ($^{28}Si^-$) ions of silicon particles in a factory test sample used for beam size specification of a NanoSIMS secondary ion mass spectrometer instrument, obtained utilizing an ionizer section according to FIG. 5.

FIG. 8A is an image using oxygen ($^{16}O^-$) ions of the factory test sample used for beam size specification of a NanoSIMS secondary ion mass spectrometer instrument, obtained utilizing an ionizer section according to FIG. 5.

FIG. 8B is an image using silicon ($^{28}Si^-$) ions of the factory test sample used for beam size specification of a NanoSIMS secondary ion mass spectrometer instrument, obtained utilizing an ionizer section according to FIG. 5.

FIG. 8C is an image using carbon ($^{12}C^-$) ions of the factory test sample used for beam size specification of a NanoSIMS secondary ion mass spectrometer instrument, obtained utilizing an ionizer section according to FIG. 5.

FIG. 10 is a secondary electron image of a holey carbon film used for particulate sample support in the NanoSIMS secondary ion mass spectrometer instrument, obtained utilizing a factory primary ion source and depicting a strong displaced ghost image.

FIG. 11 is a cross-sectional schematic illustration of a primary ion source including a metal reservoir body, a metal sealing cap, and a subassembly including a unitary graphite ionizer tube and reservoir base according to one embodiment.

FIG. 13A is a cross-sectional schematic illustration of an all-graphite primary ion source including a graphite reservoir body and a subassembly including a unitary graphite ionizer tube and externally threaded reservoir base, wherein the ionizer tube includes a distal end with an outwardly protruding conical surface and the ion source is devoid of a sealing cap, according to one embodiment.

FIG. 13B is a magnified cross-sectional schematic illustration of the distal end of the ionizer tube of FIG. 13A.

FIG. 14 illustrates a cone, showing a cone half-angle α and a complementary cone half-angle β.

FIG. 15 is a cross-sectional schematic illustration of a primary ion source including a graphite reservoir body, a male metal reservoir mounting post, and a subassembly including a unitary graphite ionizer tube and externally threaded reservoir base, wherein the ionizer tube includes a distal end with an outwardly protruding conical surface, according to one embodiment.

FIG. 16 is a cross-sectional schematic illustration of a primary ion source including a graphite reservoir body, a female metal reservoir mounting post, and a subassembly including a unitary graphite ionizer tube and externally threaded reservoir base, wherein the ionizer tube includes a distal end with an outwardly protruding conical surface, according to one embodiment.

FIG. 18A is a cross-sectional schematic view of a tip of an ion source having a tapered (e.g., conical) tip configured to transmit cesium ions through successively arranged apertures of an extraction plate and a beam stop plate, with the beam stop plate aperture having a variable diameter, and with FIG. 18A including lines showing trajectories of cesium ions.

FIG. 18B is a cross-sectional schematic view of a portion of a beam stop plate according to one embodiment, with the beam stop plate having a frustoconical extension arranged to be placed along an upstream side, and having a beam stop aperture registered with the extension and having a variable aperture with a reduced diameter along a leading edge and an increased diameter along a trailing edge.

FIG. 19 is a cross-sectional schematic illustration of an ionizer section according to another embodiment, the ionizer section including a capillary insert retained by a threaded cap, with the capillary insert having a distal end including an outwardly protruding conical surface and defining an ionizer aperture, and with the conical surface extending through an orifice defined in the threaded cap.

FIG. 20 is a plot of cesium ion fraction evaporating from a non-specific heated surface as a function of temperature.

FIG. 21 includes superimposed plots of cesium ion fraction evaporating from heated graphite (C) and tungsten (W) surfaces as a function of temperature, with addition of two vertical lines bounding a preferred useable temperature window.

FIG. 22 is a cross-sectional schematic illustration of an ionizer section similar to the ionizer section of FIG. 19, further including a refractory metal coating arranged over at least a portion of the conical surface of the distal end of the capillary insert.

FIG. 24A is a cross-sectional schematic illustration of a primary ion source according to one embodiment including a disposable graphite tube gasket with a variable diameter arranged between reservoir portions and suitable for use with a secondary mass spectrometer instrument.

FIG. 24C is a cross-sectional schematic illustration of portions of the primary ion source of FIG. 24A during a step of assembly, wherein the graphite tube gasket is pressed into the reservoir base 941 using an elongated temporary sealing nut and using a cylindrical Teflon stub fitted into the reservoir cap.

DETAILED DESCRIPTION

Figure 2:
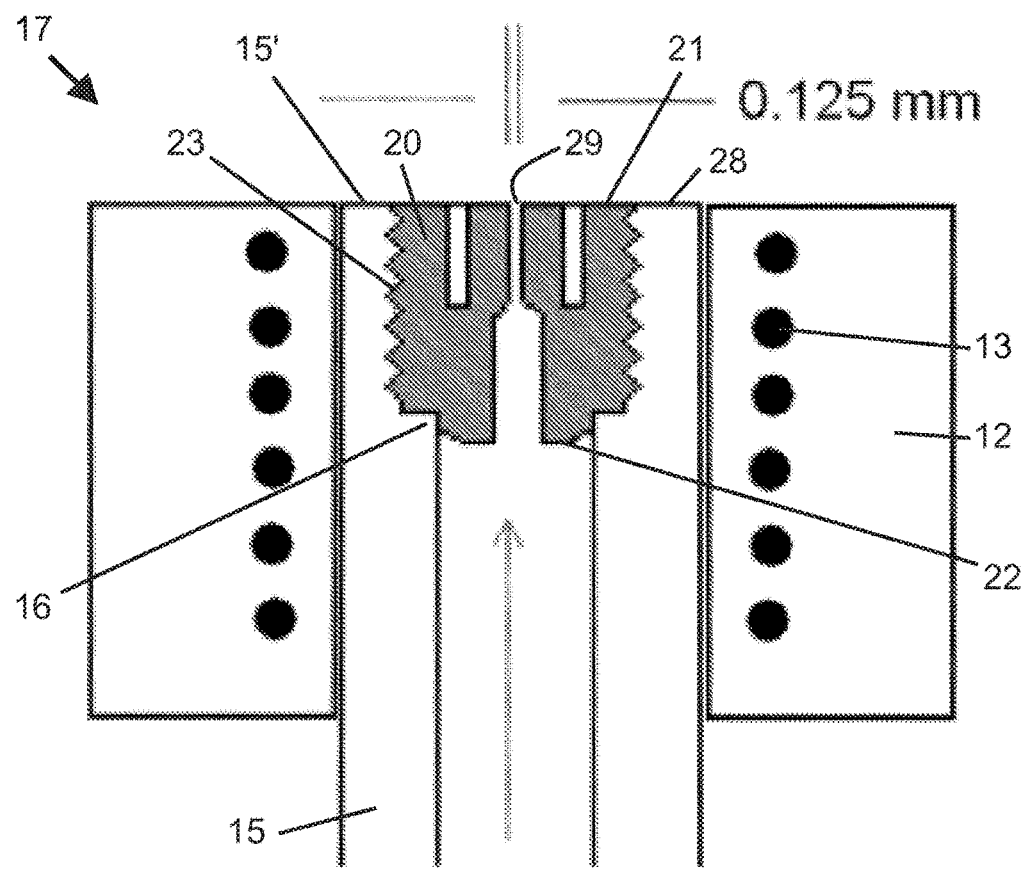
FIG. 2 illustrates an alternative ionizer section design developed around the year 2000 for use with a secondary mass spectrometer instrument.

Aspects of this disclosure relate to a primary ion source, a primary ion source subassembly, and an ion supply assembly arranged for use with a secondary ion mass spectrometer.

An ionizer section of a primary ion source for use with a secondary ion mass spectrometer according to one embodiment is shown in FIG. 3A. In such embodiment, the same reservoir and mounting structure as the factory ion source (such as shown in FIG. 1A) may be used, but the ionizer (e.g., tip) portion differs from the structures shown in FIGS. 1B-1D and FIG. 2. Rather than forming ions on a flat ionizer plate 8 as shown in FIGS. 1B-1D, the ionizer portion of FIG. 3A forms ions in a fine channel 58 terminating at an aperture 59 preferably no greater than 125 μm in diameter (or more preferably no greater than 100 μm in diameter, no greater than 75 μm in diameter, no greater than 50 μm in diameter, no greater than 25 μm in diameter, or no greater than 10 μm in diameter). Such an aperture 59 and channel 58 may be formed by any appropriate means such as (but not limited to) mechanical drilling or laser drilling through a graphite insert. Laser drilling may permit formation of smaller apertures than could practically be formed using mechanical drilling. The cesium vapor flows freely through the channel 46, as in the factory source, but the ion formation area is limited to a value much smaller than the 500 μm diameter of the ion extraction opening of the factory source.

The ionizer section of FIG. 3A includes a capillary insert 50 defining an ionizer aperture 59 and retained by a threaded cap 60 in a sealing relationship with an ionizer tube 45. The capillary insert (or plug) 50 includes a shoulder 57 arranged to abut an end of the ionizer tube 45, which includes external threads 47 arranged to cooperate with threads 65 of the cap 60. The capillary insert 50 includes a distal end 51 and a proximal end 52. In certain embodiments, the threaded cap 60 may comprise molybdenum material. The cap 60 includes a distal end 61 and an inwardly tapered (or reverse tapered) surface 64 defining an orifice registered with the ionizer aperture 59 of the capillary insert 50. To guarantee sealing and also to make the source ionizer section more easily demountable after heating, the threaded surfaces 47, 65 as well as surfaces of the capillary insert 50 contacting the end of the ionizer tube 45 and the internal surface of the threaded cap 60 may be coated with graphite powder prior to assembly. The metal swage fitting surfaces of the two parts 3, 6 of the reservoir (as shown in FIG. 1A) may also be coated with graphite, again to ensure sealing and to facilitate demounting. The ionizer section of FIG. 3A may be readily disassembled, and the graphite capillary insert 50 may be replaced by a user if it becomes damaged.

FIG. 3B is an exploded elevation view of an ion source for a secondary mass spectrometer instrument, utilizing an ionizer section 40 similar to the design of FIG. 3A. The ion source includes a heated reservoir body 33 supported by a mounting post 32, with the reservoir body 33 including an externally threaded surface 36, a beveled surface 35, and a neck portion 34 (arranged to receive the mounting post 32). In certain embodiments, the reservoir body 33 and the mounting post 32 may be configured as a single assembly 30 fabricated from a continuous material. An ionizer section 40 includes a reservoir base 41 having an ionizer tube receptacle 42, an ionizer tube 45 including external threads 47, a capillary insert 50, and an internally threaded cap 60' arranged to secure the capillary insert 50 in a sealing relationship with the ionizer tube 45. The cap 60' includes an orifice (not shown) registered with an aperture (not shown) defined in the capillary insert 50. In certain embodiments, the capillary insert 50 may be fabricated of graphite. A proximal end 45A of the ionizer tube 45 is sealed into the ionizer tube receptacle 42 of the reservoir base 41 to effect a vacuum seal that maintains integrity at the source operating temperature. A preferable sealing method uses copper metal brazing. In certain embodiments, the reservoir base 41, screw mount portion 42, and ionizer tube 45 may be fabricated of a single continuous piece of material. An internally threaded sealing nut 70 is arranged to engage the externally threaded surface 36 of the reservoir body 33 to cause a surface of the reservoir base 41 to press against the beveled surface 35 of the reservoir body 33 to enclose a reservoir composed of the reservoir body 33 and the reservoir base 41. In use, the reservoir is heated to cause cesium carbonate vapor to travel from the reservoir through the ionizer tube 45 and the aperture of the capillary insert 50, wherein the vapor is decomposed and ionized to form cesium ions.

Performance parameters for the ionizer section and primary ion source of FIGS. 3A-3B are shown in FIGS. 4A and 4B. FIG. 4A represents an image of an etched silicon test grid obtained with the factory cesium ion source, and FIG. 4B represents an image of the etched silicon test grid obtained with the novel ionizer section of FIG. 3A. FIG. 4B clearly shows sharper features (together with a noise level that was traced to incorrect sealing of the ionizer tube to the reservoir). Note in particular the bright spots scattered around the image of FIG. 4B. In FIG. 4A corresponding to use of the factory primary ion source, these features are barely visible, since such features are significantly smaller than the factory beam size. In FIG. 4B, the spots are much stronger because the beam size is now more comparable to the feature size. In FIG. 4B, the small bright spot features are more visible due to the significantly smaller beam spot size, with the beam size being more comparable to the feature size than was the case for the beam size used in FIG. 4A. It is noted that the current used with the ionizer section of FIG. 3A was 51.4 nA, about twice the current of 20.3 nA used with the factory source when these images were obtained. These currents were not measured at the test grid sample but were recorded at a test point upstream before the cesium ion beam was attenuated by a final aperture in the primary ion optical column.

FIG. 5 is a cross-sectional schematic illustration of an ionizer section according to another embodiment, the ionizer section including a capillary insert 150 defining an ionizer aperture 159 and retained by a threaded cap 160 having a different shape than the cap 60 of FIG. 3A (e.g., eliminating the reverse taper of the cap of FIG. 3A). The capillary insert (or plug) 150 includes a distal end 151 and a proximal end 152. The capillary insert 150 further includes a shoulder 157 arranged to abut an end of an ionizer tube 145, which includes external threads 147 arranged to cooperate with threads 165 of the cap 160. The capillary insert 150 includes a distal end 151 and a proximal end 152. The capillary insert 150 includes a wide channel portion 158 intermediately arranged between a channel 146 of the ionizer tube 145 and the narrow ionizer aperture 159. The cap 160 includes a flat proximal end 162 and a distal end 161 having an outwardly beveled edge 166. The cap 160 also defines an orifice 164 registered with the ionizer aperture 159, and includes a cavity containing the capillary insert 150. In certain embodiments, the capillary insert 150 comprises graphite material.

Figure 7:
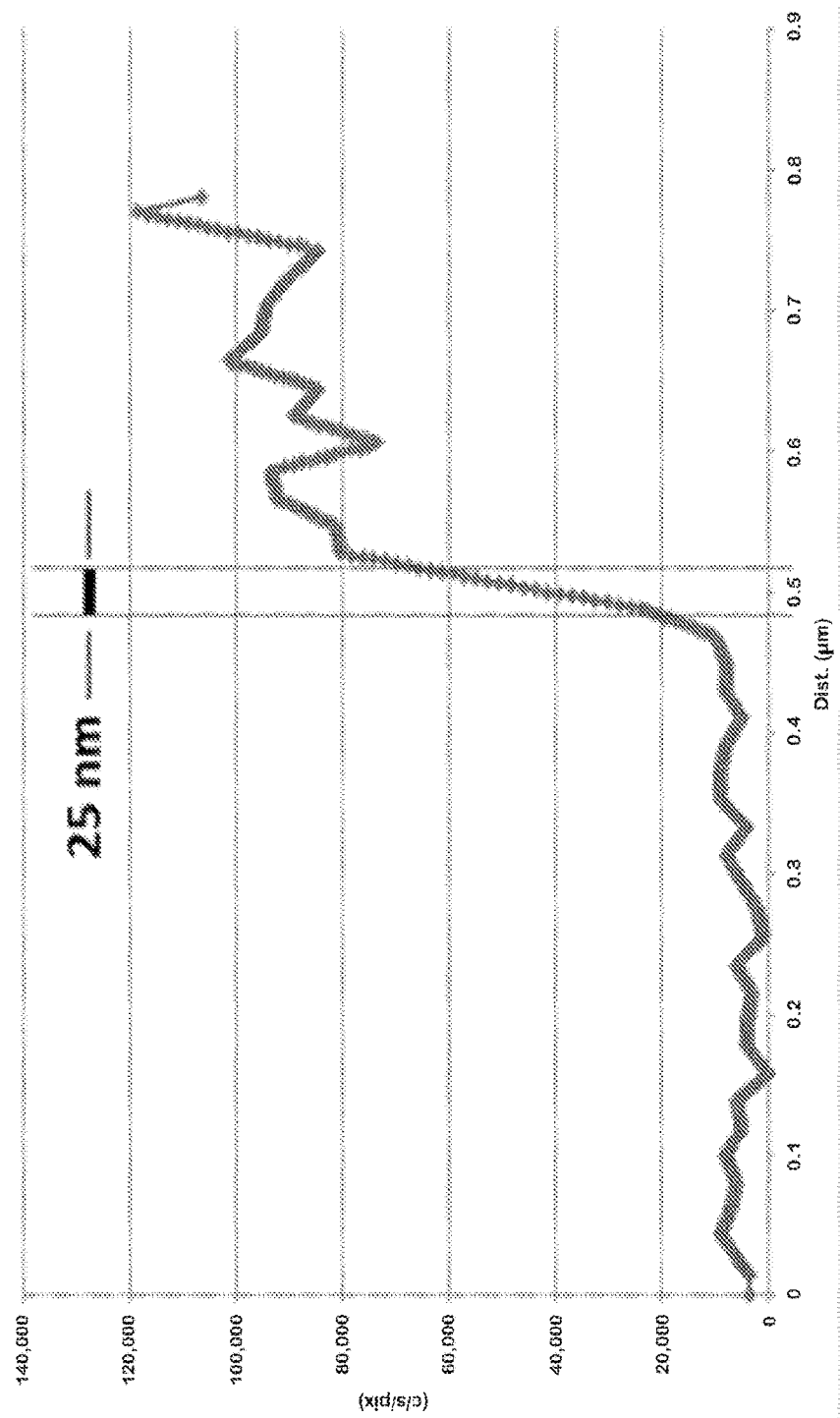
FIG. 7 is a line scan using silicon ($^{28}Si^-$) ions across a sharp-edged feature (i.e., a silicon particle identified with an arrow in FIG. 6) in the factory test sample depicted in FIG. 6.

FIG. 6 is an image made using silicon ($^{28}Si^-$) ions of silicon particles embedded in an aluminum matrix in a factory test sample used for beam size specification of a NanoSIMS secondary ion mass spectrometer instrument, obtained utilizing an ionizer section according to FIG. 5. FIG. 7 shows a line scan across a sharp-edged feature of the silicon-in-aluminum test sample supplied by Cameca also using the ionizer section according to FIG. 5. Criteria for beam size differ. The most common criterion (and that used by the factory) is the distance over which the ion signal varies from 16% to 84% of maximum. The superimposed scale bar in FIG. 7 is 25 nm wide. It roughly spans the 16-84% range of the scan. The 25 nm scale bar indicates that the beam size was close to this value. Notably, the beam current (measured at the sample) for this scan was 1 pA—a current value four times the typical factory current value. This increased current is beneficial in multiple respects: not only does it offer a major increase (4×) in analysis speed, but also it suggests that by sacrificing more current an even smaller ion beam may be achieved.

Figure 9:
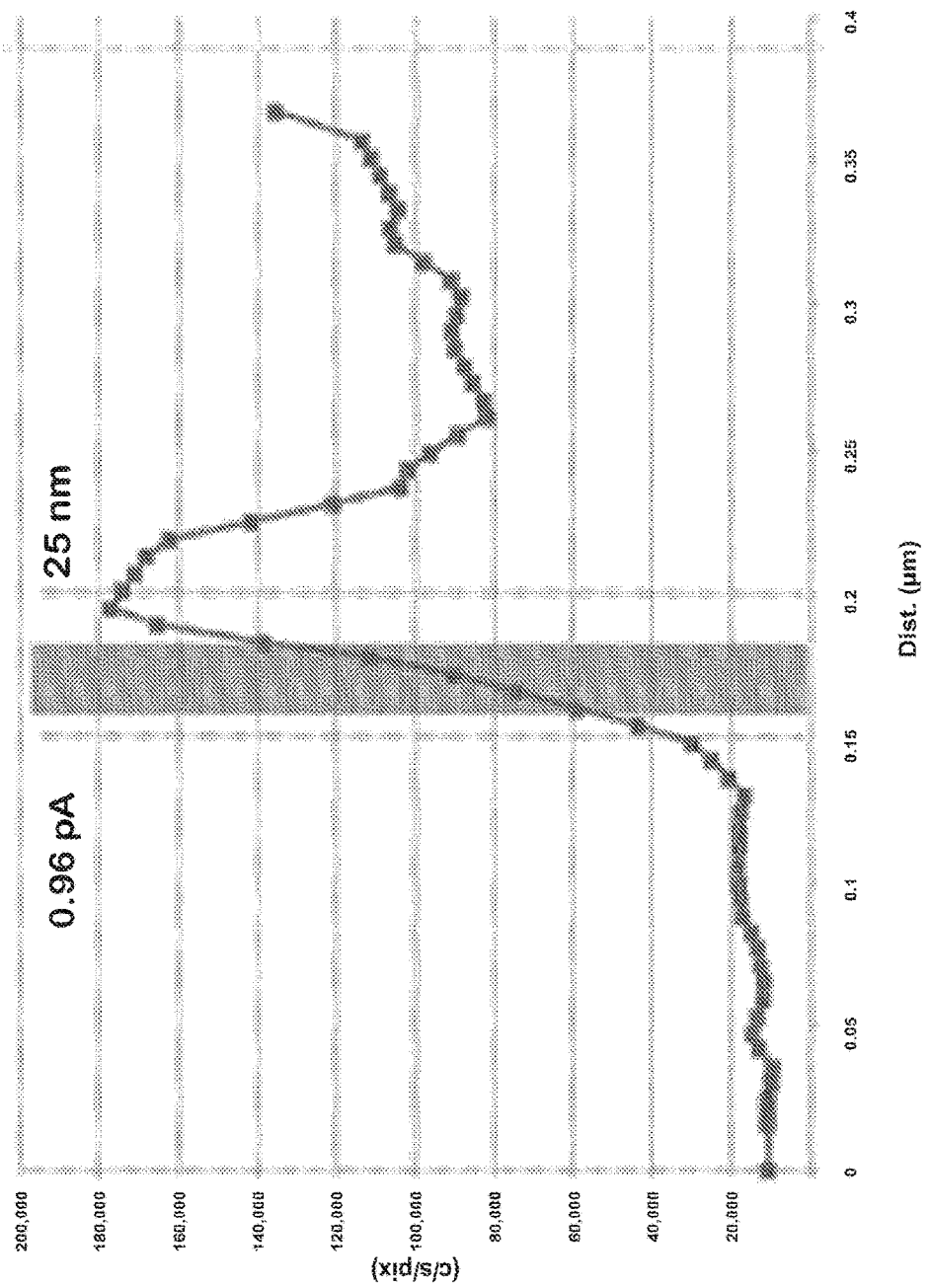
FIG. 9 is a line scan across a feature in the oxygen ($^{16}O^-$) ion image arrowed in the factory test sample depicted in FIG. 8A.

FIGS. 8A-8C provide images of oxygen, silicon, and carbon obtained utilizing an ionizer section according to FIG. 5. FIG. 8A is an image made using oxygen ($^{16}O^-$) ions in the silicon-in-aluminum factory test sample used for beam size specification of a NanoSIMS secondary ion mass spectrometer instrument. FIG. 8B is an image made using silicon ($^{28}Si$) ions in the silicon-in-aluminum factory test sample used for beam size specification of a NanoSIMS secondary ion mass spectrometer instrument. FIG. 8C is an image made using carbon ($^{12}C^-$) ions in the silicon-in-aluminum factory test sample used for beam size specification of a NanoSIMS secondary ion mass spectrometer instrument. The images of FIGS. 8A-8C were taken several months after the image of FIG. 6. FIG. 9 is a line scan across a small feature in the oxygen ($^{16}O^-$) ion image of the factory test sample depicted in FIG. 8A. A line scan across a small feature in the oxygen ion image of FIG. 8A again indicates a resolution close to 25 nm, corresponding to the shaded vertical scale bar. The vertical lines to either side of the scale bar are spaced 50 nm apart.

Figure 10:
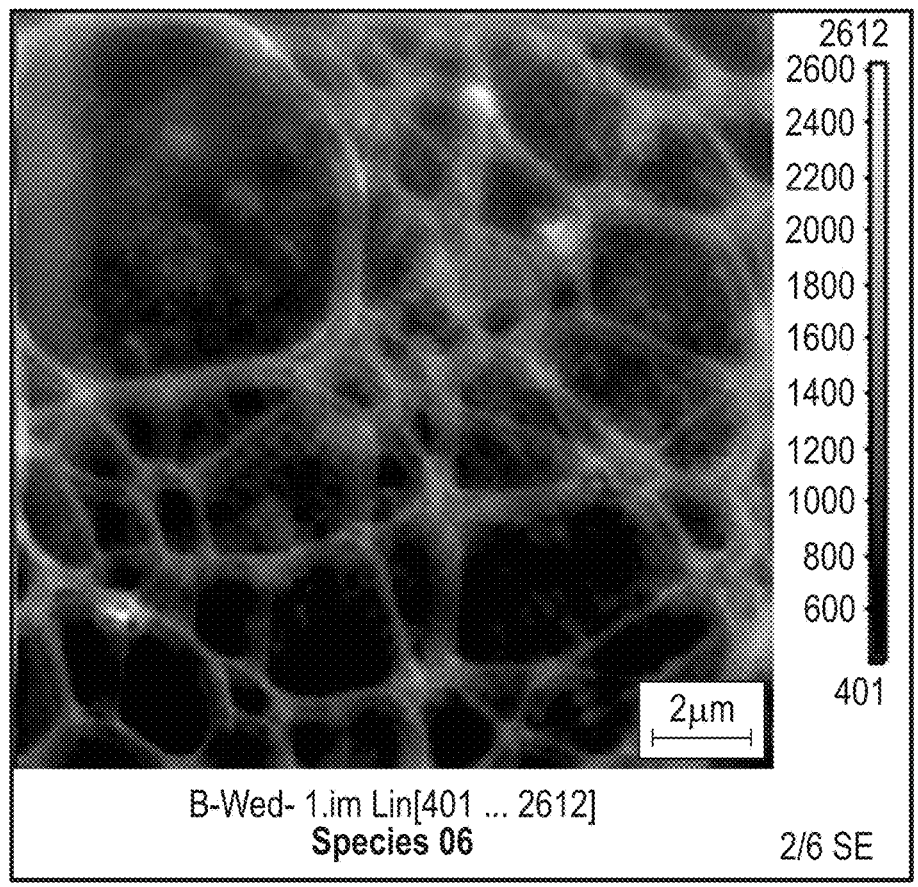
FIG. 10 illustrates the ionizer section of FIG. 1B, showing the intended (or design objective) operation with intended trajectory of cesium ions.

Note, however, a difference between the images of FIGS. 8A-8C versus the image of FIG. 6. While the images of FIGS. 8A-8C are crisp in all directions, FIG. 6 exhibits "ghost" images displaced to the right of, and slightly above, each feature. This is evidence of a second, weaker "ghost" ion beam that is displaced from the main beam. Further evidence of a "ghost" ion beam is shown in FIG. 10. FIG. 10 is a secondary electron image of a "holey" carbon film used to support particulate samples in the NanoSIMS. The secondary electrons are generated by the focused cesium ion beam together with negative ions and similarly reflect the ion beam size. The image of FIG. 10 was obtained utilizing a factory primary ion source and depicts a strong displaced (and undesirable) ghost image. The ghost image is manifested as haloed (e.g., blurred and displaced) boundaries between adjacent features. The mechanism for production of ghost beams is discussed herein (below) in connection with FIGS. 17A-17C, and at least certain embodiments described herein include features intended to reduce or eliminate presence of ghost beams.

A primary ion source for use with a secondary ion mass spectrometer according to another embodiment is shown in FIG. 11. The entire ionizer section (or ionizer subassembly) 240 of the source is fabricated from a single unitary piece of graphite (or alternatively from a graphite-containing material), including a reservoir base 241 (embodying half of the reservoir) and an ionizer tube 245 extending outward from the reservoir base 241. Such unitary fabrication avoids any possibility of cesium vapor leakage at the various joins of the ionizer section 240 and simplifies the design and machining. The ionizer subassembly 240 includes an ionizer tube 245 defining a passage 246, with a distal end 251 of the ionizer tube 245 defining an ionizer aperture 259. In certain embodiments, the ionizer aperture 259 has a reduced diameter in comparison to a nominal or average diameter of the passage 246 within the ionizer tube 245. The ionizer aperture 259 is preferably no greater than 125 µm in diameter, no greater than 100 µm in diameter, no greater than 75 µm in diameter, no greater than 50 µm in diameter, no greater than 25 µm in diameter, or no greater than 10 µm in diameter, and may be defined by mechanical drilling or laser drilling. In certain embodiments, the ionizer aperture 259 may be formed by any appropriate means such as (but not limited to) mechanical drilling or laser drilling through the distal end 251 of the tube 245. In certain embodiments, an ionizer aperture may be defined in a graphite capillary insert (not shown). A proximal section 243 of the ionizer tube 245 extends through the reservoir base 241 and terminates at a proximal end 245A. The proximal section 243 of the ionizer tube 245 in combination with sidewalls 244 of the reservoir base 241 bound an annular recess 248 that is arranged to be exposed to a cylindrical cavity 238 defined in a reservoir body 233. The reservoir base 241 further includes a radially-extending shoulder or lip portion 249 arranged to abut a beveled surface portion 235 of the sidewalls 237 of the reservoir body 233. The reservoir body 233 includes sidewalls 237 with a threaded outer surface 236, and a mounting post 232 is affixed to the reservoir body 233. A sealing nut 270 is arranged to retain the reservoir base 241 against the reservoir body 233 to seal the cylindrical cavity 238 therebetween. The sealing nut 270 includes a medial portion 271 arranged to contact the shoulder or lip portion 249 of the reservoir body 233, and includes a sidewall 276 with a threaded inner surface 277 arranged to engage the threaded outer surface 236 of the reservoir body 233. As noted previously, the swage-type seal between the two molybdenum reservoir portions utilized with the factory source requires close control of the sealing force, and is not designed to be demountable, so an ion source cannot be reused. An improved sealing approach is permitted using the primary ion source depicted in FIG. 11, since the ionizer subassembly 240 of FIG. 11 is fabricated of relatively soft graphite. A sharp beveled edge at the distal end of the beveled surface portion 235 of the reservoir body 233 is forced to bite into the graphite shoulder or lip portion 249 of the reservoir base 241 by tightening the sealing nut 270, thereby making a good seal. In a preferred sealing approach, the exterior wall of the graphite reservoir base 244 is tapered (e.g., with a taper angle preferably in a range of 1-5 degrees, or more preferably in a range of 2-3 degrees), and sized so that only a portion of the tapered surface is easily insertable into the reservoir body 233, but then must be forced fully in by tightening the sealing nut 270, thereby allowing the reservoir body 233 to cut into the tapered surface of the exterior wall of the graphite reservoir base 244 and effect a seal.

Figure 12:
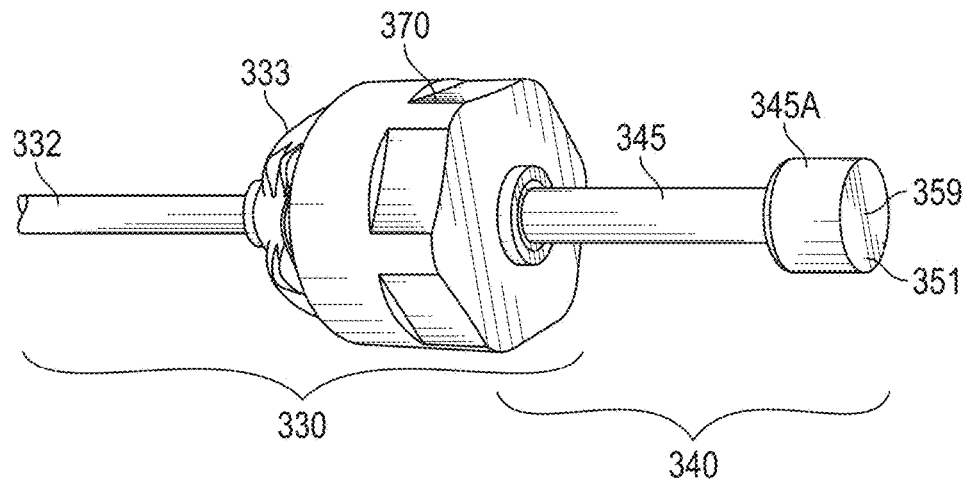
FIG. 12 is a photograph of a primary ion source according to one embodiment and including components similar to the design of FIG. 11.

FIG. 12 is a photograph of a primary ion source according to one embodiment and including components similar to the design of FIG. 11. An ionizer subassembly 340 includes a ionizer tube 345, a reservoir base (not shown), an ionizer tube end portion 345A, and an aperture 351 defined in a distal surface 359 all fabricated from a unitary piece of graphite material. The primary ion source further includes a mounting post 332 affixed to a reservoir body 333, with an internally threaded sealing nut 370 arranged to engage the ionizer subassembly 340 with the reservoir body 333. In certain embodiments, the reservoir body 333 and the mounting post 332 may be provided as a subassembly 330 embodying a continuous single piece of material.

In an alternative embodiment, a graphite ionizer subassembly may be designed with a bevel that is forced against a sharp metal edge to form a seal, similar to the apparatus shown in FIG. 1A, with a compressive force being applied using an external nut.

Sealing of an all graphite source (e.g., including a unitary graphite ionizer tube and reservoir base, and a graphite reservoir body) may be accomplished according to one of the following techniques.

In a first sealing technique, screw threads may be cut into the interior and exterior of the two reservoir portions (reservoir base and reservoir body) and the portions simply screwed together. Such technique places relatively little mechanical stress on either graphite piece. Friction of the graphite screw threads as they are tightened will rub off any high spots and ensure a surface-to-surface seal. In certain embodiments, the threads can also be lubricated with graphite powder that will help assure a seal.

In a second sealing technique, a slight bevel may be made at the top of the interior screw thread and the exterior surface edge is forced against this bevel by the screw threads.

In a third sealing technique, one of the two reservoir portions may be beveled and the two portions may be forced together by exterior metal threaded pieces.

The use of graphite as a construction material greatly improves the reusability of a primary ion source. The metal factory ion source is not intended to be reusable. When the cesium carbonate reservoir is exhausted, or when the ionizer is damaged (e.g., by excessive heat or by backstreaming ions produced by the cesium beam striking surfaces in the primary ion column), at present a user's primary remedy is to discard the primary ion source and purchase a new primary ion source from the manufacturer. Reusable reservoir ion sources disclosed herein are intended to permit a user to refill and reuse the source so long as the ionizer orifice remains intact, at the expense of a replaceable graphite double-taper gasket. If the orifice portion of the source is damaged, it alone can be replaced. In the metal design with the graphite ionizer insert, the insert and its metal screw cap will be replaceable items, and spares may be supplied with purchase.

In certain embodiments, a graphite ionizer subassembly may directly engage a reservoir base without requiring use of a sealing nut.

FIG. 13A illustrates an all-graphite primary ion source according to one embodiment. An ionizer subassembly 440 includes a ionizer tube 445 and a reservoir base 441 fabricated from a unitary piece of graphite material (or other graphite-containing material). The ionizer tube 445 defines a passage 446, with a distal end of the ionizer tube 445 including a conical or frustoconical surface 451 and defining an ionizer aperture 459 having a reduced diameter in comparison to a nominal or average diameter of the passage 446 within the ionizer tube 445. A proximal section 443 of the ionizer tube 445 extends through the reservoir base 441 and terminates at a proximal end 445A. The proximal section 443 of the ionizer tube 445 in combination with externally threaded sidewalls 444 of reservoir base 441 bound an annular recess 448 that is arranged to be exposed to a cylindrical cavity 438 defined in a reservoir body 433. The externally threaded sidewall 444 of the reservoir base 441 is arranged to engage an internally threaded surface 436 of a sidewall 437 of the reservoir body 433. The reservoir body 433 and a mounting post 432 are provided as a subassembly 430 embodying a continuous single piece of graphite (or graphite-containing) material. The two subassemblies 430, 440 are separable to allow loading of cesium carbonate or other cesium source material into the reservoir cavity 438.

FIG. 13B is a magnified cross-sectional schematic illustration of the distal end of the ionizer tube 445 of FIG. 13A, showing the conical or frustoconical surface 451 and the ionizer aperture 459. The ionizer aperture 459, which has a reduced diameter in comparison to a nominal or average diameter of the passage 446 within the ionizer tube 445, extends through a central axis (or apex) of the conical or frustoconical surface 451.

FIG. 14 illustrates a cone, showing a cone half-angle α and a complementary cone half-angle β. Comparing the cone of FIG. 14 to the distal end of the ionizer tube shown in FIG. 13B, the ionizer aperture 459 of FIG. 13B extends through a central axis (or apex) of the conical or frustoconical surface 451, and such surface 451 corresponds to the sidewall of the cone of FIG. 14. In certain embodiments, the conical or frustoconical surface 451 depicted in FIGS. 13A-13B comprises a complementary conical half-angle in a range of from 6 to 45 degrees, or in a range of from 10 to 40 degrees, or in a range of from 15 to 35 degrees, or in a range of from 20 to 30 degrees. Such angular ranges may apply to other conical or frustoconical surfaces proximate to ionizer apertures as disclosed herein.

Since a graphite mounting post 432 as illustrated in FIG. 13A may be rather fragile, in certain embodiments, a mounting post may be fabricated of metal (e.g., molybdenum) and arranged to be affixed (e.g., via a threaded connection) to a graphite reservoir body. Two alternative threaded connections between a mounting post and a reservoir body are shown in FIGS. 15 and 16.

FIG. 15 is a cross-sectional schematic illustration of a primary ion source including a graphite reservoir body 533, a (male) metal reservoir mounting post 522, and a subassembly 540 including a unitary graphite ionizer tube 545 and an externally threaded reservoir base 541, wherein the ionizer tube 545 includes an internal passage 546 and includes a distal end with an outwardly protruding conical or frustoconical surface 551 defining an ionizer aperture 559. A proximal section 543 of the ionizer tube 545 extends through the reservoir base 541 and terminates at a proximal end 545A. The proximal section 543 of the ionizer tube 545 in combination with externally threaded sidewalls 544 of the reservoir base 541 bound an annular recess 548 that is arranged to be exposed to a cylindrical cavity 538 defined in the reservoir body 533. The externally threaded sidewall 544 of the reservoir base 541 is arranged to engage an internally threaded surface 536 of a sidewall 537 of the reservoir body 533. The mounting post 522 includes a radially extending flange portion 523 and an externally threaded protruding portion 524 is arranged to engage an internally threaded recess 534 of the reservoir body 533. In certain embodiments, the mounting post 522 may be fabricated of metal (e.g., molybdenum) and the reservoir body 533 may be fabricated of graphite. The subassembly 540 is separable from the reservoir body 533 to allow loading of cesium carbonate or other cesium source material into the reservoir cavity 538.

FIG. 16 is a cross-sectional schematic illustration of a primary ion source including a graphite reservoir body 633, a (female) metal reservoir mounting post 622, and a subassembly 640 including a unitary graphite ionizer tube 645 and an externally threaded reservoir base 641, wherein the ionizer tube 645 includes an internal passage 646 and includes a distal end with an outwardly protruding conical or frustoconical surface 651 defining an ionizer aperture 659. A proximal section 643 of the ionizer tube 645 extends through the reservoir base 641 and terminates at a proximal end 645A. The proximal section 643 of the ionizer tube 645 in combination with externally threaded sidewalls 644 of reservoir base 641 bound an annular recess 648 that is arranged to be exposed to a cylindrical cavity 638 defined in a reservoir body 633. The externally threaded sidewall 644 of the reservoir base 641 is arranged to engage an internally threaded surface 636 of a sidewall 637 of the reservoir body 633. A mounting post 622 includes a screw mount portion 625 defining an internally threaded recess 626 arranged to engage an externally threaded protruding portion 634 of the reservoir body 633. In certain embodiments, the mounting post 622 may be fabricated of metal (e.g., molybdenum) and the reservoir body 633 may be fabricated of graphite. The subassembly 640 is separable from the reservoir body 633 to allow loading of cesium carbonate or other cesium source material into the reservoir cavity 638.

Figure 17C:
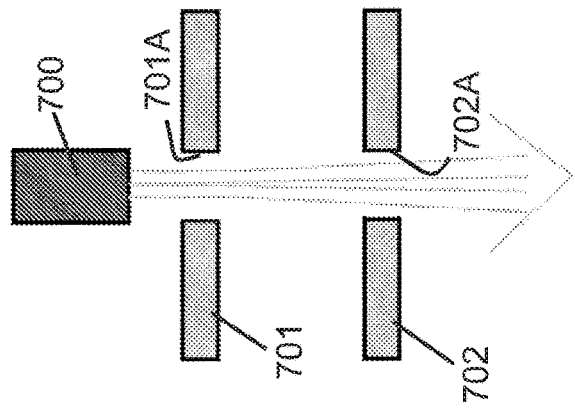
FIGS. 17A-17C are cross-sectional schematic views of an ion source configured to transmit cesium ions through successively arranged apertures of an extraction plate and a beam stop, with arrows showing trajectories of cesium ions, showing the mechanism of ghost beam formation.
Figure 17B:
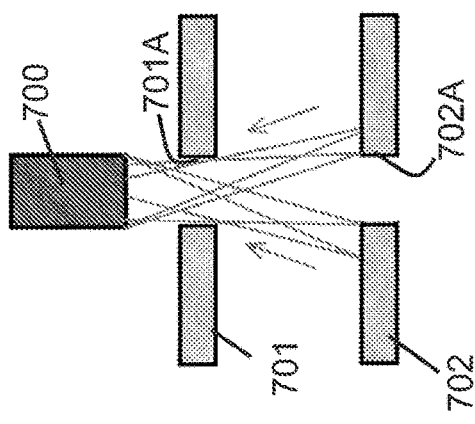
Figure 17A:
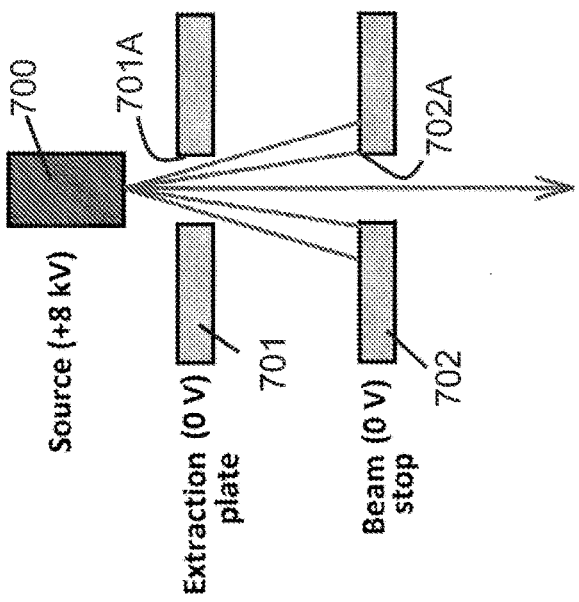

The mechanism for ghost beam formation will now be described. FIGS. 17A-17C are cross-sectional schematic views of an ion source 700 configured to transmit cesium ions through successively arranged apertures 701A, 702A of an extraction plate 701 and a beam stop plate 702, with arrows showing trajectories of cesium ions. In FIG. 17A, Cs+ ions from the ion source 700 spread, and some ions impact on the beam stop plate 702 and implant cesium into the surface of the beam stop plate 702. In FIG. 17B, subsequent Cs+ ion impacts on the beam stop plate 702 sputter the implanted Cs as neutral atoms, which drift back to the hot ionizer. In FIG. 17C, the re-ionized Cs+ ions are accelerated through the beam stop aperture 702A. A significant fraction of the initially formed Cs+ ion beam spreads to hit the (e.g., molybdenum) beam stop plate 702, which is placed specifically to intercept this spreading beam and protect downstream lens elements (not shown). These impacting ions can sputter negative ions from the beam stop plate 702 that can be accelerated back to the ion source 700, resulting in sputtering of positive ions from a surface of the ion source 700. This effect is probably minor as the electron affinity of the beam stop metal is low so negative ion yields are small. A more significant effect is that the implanted cesium is resputtered. At steady state, one cesium is sputtered for every impacting ion. Due to the buildup of cesium in the surface of the beam stop plate 702, the ionization probability of the resputtered cesium is low, ~50% or less. Although resputtered Cs+ ions cannot return to the positively-biased ionizer, neutral cesium atoms can readily return to the ionizer. A portion of the neutral flux of sputtered cesium (shown in FIG. 17B) can re-impact the front surface of the hot ion source 700, where it will be ionized with ~100% efficiency. This produces a ghost beam of Cs+ ions (shown in FIG. 17C) that travels down the column and can be focused by the ion lenses. The effect of the acceleration field and the field penetration through the extraction plate 701 is to make the ghost beam appear to come from a virtual object plane behind the ionizer face. This beam will be out of focus at the sample and can produce a weak halo that may be hard to detect, but that can generate ions from beyond the small area impacted by the main beam and produce erroneous results. The preceding discussion is valid for all ionizer geometries. The combination of flat and convex surfaces in the Cameca factory source can produce several ghost beams with different apparent points of origin and focusing properties.

Applicant has developed three approaches to reducing or eliminating ghost beams in primary ion sources for secondary ion mass spectrometers. A first approach involves shaping an ionizer surface to prevent ghost ions from passing through beam stop aperture. A second approach involves shaping a beam stop so that generation of resputtered cesium atoms that hit the ionizer is minimized. A third approach involves tailoring the chemistry and temperature of an ionizer surface so that the area impacted by the resputtered cesium does not result in re-ionization of these resputtered cesium atoms. The preceding approaches may be used separately or in combination in certain embodiments.

FIG. 18A is a cross-sectional schematic view of a tip of an ion source 700 having a distal end with a tapered (e.g., conical or frustoconical) surface 710 including a ionizer aperture 709, configured to transmit cesium ions through successively arranged orifices 711A, 712B of an extraction plate 711 and a beam stop plate 712. FIG. 18A includes ion-optical simulation of the effect of tapering the ionizer front surface 710 by 30 degrees. Because ions formed on the tapered surface 710 are initially accelerated normal to the surface that they leave, ions from this tapered surface 710 (even ions formed very close to the tip of the cone as in FIG. 18A) cannot pass through the beam stop plate orifice 712B if the angle of the tapered surface 710 is sufficiently large. The beam stop plate orifice 712B includes a variable diameter, with a reduced diameter leading edge 713-1 proximate to the primary ion source 700, and with an increased diameter trailing edge 713-2 distal from the primary ion source 700. In certain embodiments, the beam stop plate orifice 712B comprises a frustoconical cross-sectional shape. The tapered (e.g., conical or frustoconical) shape of the tapered surface 710 of the ion source 700 reduces or eliminates the ability of sputter-deposited Cs ions emanating from the tapered surface 710 to pass through the successively arranged orifices 711A, 712B of an extraction plate 711 and a beam stop plate 712. Lines 719 proximate to the tapered surface 710 are tangent to potential directions of Cs ions emanating from the source 700, including ions formed from resputtered Cs. In certain embodiments, the conical or frustoconical surface 710 comprises a complementary conical half-angle in a range of from 6 to 45 degrees, or in a range of from 10 to 40 degrees, or in a range of from 15 to 35 degrees, or in a range of from 20 to 30 degrees. Such angular ranges apply to conical or frustoconical surfaces disclosed herein.

FIG. 18B is a cross-section of a modified beam stop plate 722 according to one embodiment, with the beam stop plate 722 including a frustoconical extension 724 arranged to be placed on a side proximate to an upstream ionizer (e.g., a primary ion source as shown in FIG. 18A). The beam stop plate 722 includes an aperture 722B registered with the frustoconical extension 724, with the aperture 722B having a variable diameter including a reduced diameter leading edge 723-1 proximate to an upstream primary ion source, and with an increased diameter trailing edge 723-2 distal from the upstream primary ion source. The frustoconical extension 724 is designed to ensure that cesium ions spreading out from an ionizer aperture will strike the extension surface 724A at glancing angles. At these glancing angles, the majority of the impacting cesium ions will not implant into the beam stop plate 722 proximate to the aperture 722B, but instead will scatter forward and outward and eventually come to rest on or in the beam stop material at points too distant for any resputtered cesium to return to a surface of an upstream primary ion source. Any cesium that does become implanted in the beam stop material at the initial impact has a high probability of being resputtered in a forward direction and, again, coming to rest on or in the beam stop material at points too distant for any resputtered cesium to return to a surface of the upstream primary ion source. Additionally, the low concentration of implanted cesium in the initially impacted extension surface 724A of the beam stop plate 722 will minimize the work function reduction in the impacted surface. Any cesium resputtered from this high work function surface will leave the surface predominantly as positive cesium ions, which cannot return to the positively-biased upstream primary ion source.

As will be appreciated from the foregoing description of FIGS. 18A-18B, some or all of the following parameters may be selected to prevent passage through the beam stop plate orifice of cesium ions other than cesium ions emanating directly from the ionizer aperture: (a) shape of the distal end portion of the ionizer, (b) materials of the distal end portion of the ionizer, and (c) size and shape of the beam stop plate orifice.

Ionizer subassemblies including distal ends with conical or frustoconical surfaces of ionizer tubes were illustrated in FIGS. 13A, 15, and 16. In certain embodiments, graphite capillary inserts may include conical or frustoconical surfaces proximate to ionizer apertures.

FIG. 19 illustrates an ionizer section according to one embodiment, the ionizer section including a capillary insert 750 (e.g., comprising graphite or graphite-containing material) retained by a threaded cap 760, with the capillary insert 750 having a distal end including an outwardly protruding conical surface 751 and defining an ionizer aperture 759, and with the conical surface 751 extending through an orifice 764 defined in a medial portion 761 along a distal end of the threaded cap 760. The capillary insert (or plug) 750 includes a distal end (conical surface) 751 and a proximal end 752. The capillary insert 750 further includes a shoulder 757 arranged to abut an end of an ionizer tube 745, which includes external threads 747 arranged to cooperate with threads 765 of the cap 760. The capillary insert 750 includes a wide channel portion 758 intermediately arranged between a channel 746 of the ionizer tube 745 and the narrow ionizer aperture 759. The cap 760 includes a proximal end portion 762 and an outwardly beveled edge 766. The orifice 764 of the cap 760 is registered with the ionizer aperture 759, and includes a cavity containing the capillary insert 750. In certain embodiments, the ionizer tube 745 and the cap 760 comprise at least one metal (e.g., molybdenum or tungsten), and the capillary insert 750 comprises graphite. In certain embodiments, the conical surface 751 may be frustoconical in shape. Since any cesium ions present on the conical surface 751 will be accelerated normal to the surface 751, presence of an outwardly protruding conical or frustoconical surface with a sufficient angle (e.g., a complementary conical half-angle in a range of from 6 to 45 degrees, or in a range of from 10 to 40 degrees, or in a range of from 15 to 35 degrees, or in a range of from 20 to 30 degrees) will reduce likelihood that any cesium ions ionized from such surface will transit through a beam stop aperture (such as shown in FIGS. 18A-18B).

Effects of ionizer surface material tailoring and control of ionization temperature will be introduced before discussing further embodiments involving presence of a refractory metal coating or refractory metal sheath arranged over at least a portion of a conical or frustoconical ionizer surface.

FIG. 20 is a plot of cesium ion fraction ($\alpha$) evaporating from a heated surface as a function of temperature. The peak ion fraction is close to 1. Both graphite and tungsten have electron work functions (potential barriers to electron escape) of around 4.5 eV for clean surfaces, which is higher than the ionization potential of cesium (3.9 eV). Thus, it is energetically more favorable for cesium to evaporate from these clean, high work-function, surfaces as a positive ion, at any temperature. Cesium is adsorbed as a positive ion. As an absorbed cesium ion moves away from the surface, although the energy of the empty valence level in the atom drops, it never falls below the Fermi level in the metal and there is no possibility that an electron from the metal can tunnel into the cesium ion to neutralize it. For cesium evaporating from an otherwise clean surface, the curve in FIG. 20 should be flat at all temperatures (more precisely, it should drop slightly with temperature at the higher temperatures because evaporation as a neutral is an activated process that becomes more probable at higher temperature). The reason for the sharp onset in the curve is that, for a given cesium flux to the surface, at lower temperatures the cesium does not evaporate fast enough as either ions or neutrals and instead builds up on the surface. This lowers the work function drastically (the minimum work function for a cesium coverage of about 10-20% of a monolayer is as low as 1.5 eV, much lower than the cesium ionization potential), and thus the emission of ions is suppressed due to electron tunneling from the surface. For a given flux of cesium to the surface, the temperature must be high enough to maintain the cesium coverage at a low enough level such that the work function does not fall below 3.9 eV. For a tungsten surface, the sharp onset of ionization occurs at around 1200 C when the cesium coverage drops low enough for the clean surface work function to exist. Applicant has observed that graphite ionizers disclosed herein operate at a lower temperature (estimated by the heating current) than do the tungsten ionizers, possibly as low as 900 C. This is believed to be due to the heat of adsorption of cesium on carbon being significantly lower than on tungsten, so that significantly higher temperature is required to keep the surface of the tungsten ionizer cesium-free. This effect offers a means to suppress ghost beam formation at metal parts of ionizers, by operating at a temperature sufficient for ionization on carbon but too low for appreciable ionization from tungsten (or molybdenum, which is believed to behave similarly to tungsten). FIG. 21 includes superimposed plots of cesium ion fraction evaporating from heated graphite (C) and tungsten (W) surfaces as a function of temperature, identifying a preferred usable temperature "window" preferably bounded by the two solid vertical lines. The $T_0$ value for graphite is estimated to be around 900° C.

Taking into account the foregoing discussion of ionizer surface material tailoring and control of ionization temperature, in certain embodiments, a refractory metal coating or refractory metal sheath may be arranged over at least a portion of a graphite ionizer surface, which preferably has a conical or frustoconical shape. Heating of the graphite ionizer surface to around 900° C. is sufficient to ionize cesium ions, but such temperature is not sufficiently high to ionize cesium present on any refractory metal (e.g., tungsten or molybdenum) surfaces.

FIG. 22 is a cross-sectional schematic illustration of an ionizer section similar to the ionizer section of FIG. 19, further including a refractory metal coating 769 arranged over at least a portion of the conical surface 751 of the distal end of the capillary insert 750. All other elements of FIG. 22 are identical to the elements described in connection with FIG. 19, so further discussion of such elements is omitted for brevity. The refractory metal coating may be deposited by sputtering or any other suitable technique over the conical surface 751. In certain embodiments, the conical surface 751 may be frustoconical in shape. In certain embodiments, substantially all outwardly facing (e.g., exposed) portions of the conical surface 751 are coated with refractory metal (e.g., tungsten and/or molybdenum). In certain embodiments, the applied metal coating 769 may react with graphite of the capillary insert to form a metal carbide. In certain embodiments, the applied metal coating 769 covers more than 80%, more than 90%, or more than 95% of the conical (or frustoconical) surface 751 of the capillary insert 750.

Figure 23:
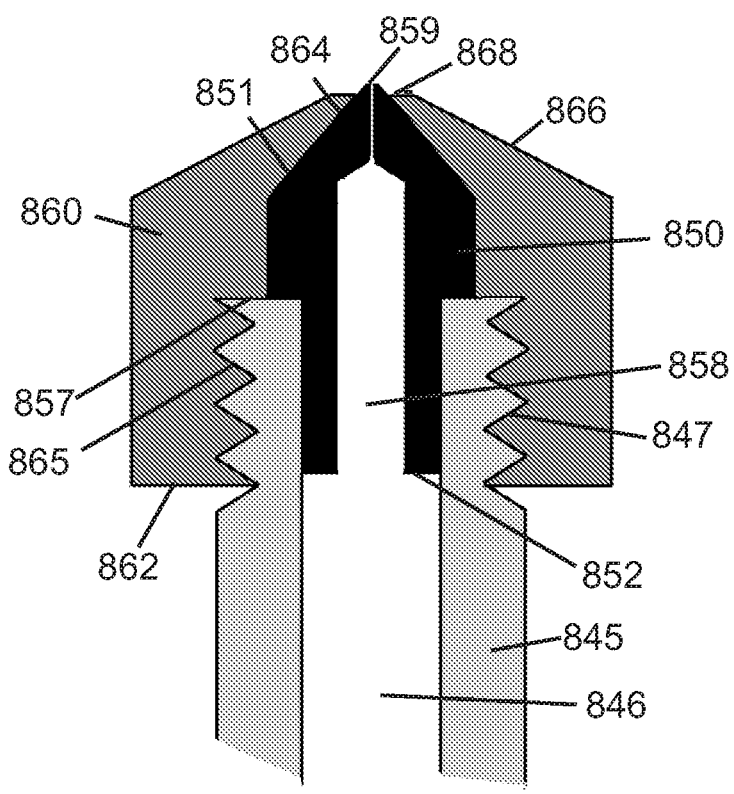
FIG. 23 is a cross-sectional schematic illustration of an ionizer section similar to the ionizer section of FIG. 19, but wherein the cap includes a tapered distal end arranged to form a refractory metal sheath over at least a portion of the conical surface of the distal end of the capillary insert.

FIG. 23 is a cross-sectional schematic illustration of an ionizer section similar to the ionizer section of FIG. 19, but wherein the cap 860 includes a tapered distal end 866 arranged to form a refractory metal sheath over at least a portion of the outwardly protruding conical surface 851 of the distal end of the capillary insert 850. The capillary insert 850 defines an ionizer aperture 859, with the conical surface 851 extending through an orifice 864 defined in a medial portion 868 along a distal end of the threaded cap 860. The capillary insert (or plug) 850 includes a distal end (conical surface) 851 and a proximal end 852. The capillary insert 850 further includes a shoulder 857 arranged to abut an end of an ionizer tube 845, which includes external threads 847 arranged to cooperate with threads 865 of the cap 860. The capillary insert 850 includes a proximal end portion 862, and includes wide channel portion 858 intermediately arranged between a channel 846 of the ionizer tube 845 and the narrow ionizer aperture 859. The orifice 864 of the cap 860 is registered with the ionizer aperture 859, and includes a cavity containing the capillary insert 850. In certain embodiments, the ionizer tube 845 and the cap 860 comprise at least one refractory metal (e.g., molybdenum or tungsten), and the capillary insert 850 comprises graphite. In certain embodiments, the conical surface 851 may be frustoconical in shape. In certain embodiments, the cap 860 covers more than 80%, more than 90%, or more than 95% of the conical (or frustoconical) surface 851 of the capillary insert 850.

Certain embodiments are directed to an improved primary ion source arranged for use with a secondary ion mass spectrometer including a novel reservoir sealing system using a disposable tubular graphite gasket. As noted previously herein, the reservoir of a factory ion source is sealed using a swage design in which two shaped molybdenum surfaces (bounding a reservoir) are forced into contact with one another by application of a screw cap. The torque required to achieve a seal with a fairly hard metal such as molybdenum is quite high, and the torque parameters must be carefully controlled to achieve a balance between sealing and avoiding cracking of the metal. Molybdenum is embrittled at the reservoir temperature and the source body cannot be reused because re-torquing the joint causes cracking. To overcome challenges with sealing metal portions of a reservoir, a disposable tubular graphite gasket has been developed to enable low torque operation while providing excellent sealing properties.

Figure 24B:
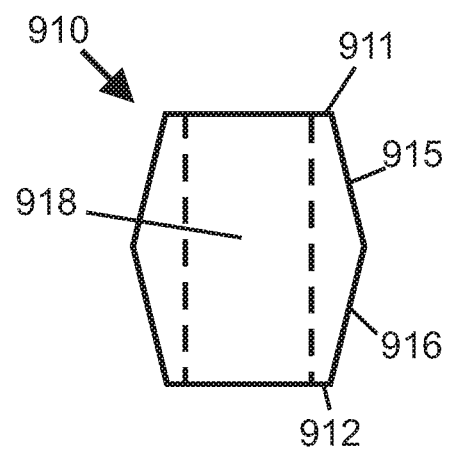
FIG. 24B is a schematic cross-sectional illustration of a variable diameter graphite tube gasket, depicting a maximum outer diameter at an intermediate point and a minimum outer diameter along two ends, with exaggerated diametric variation.

FIG. 24A is a cross-sectional schematic illustration of a primary ion source according to one embodiment including a disposable graphite tube gasket 910 with a variable diameter arranged between a metal reservoir body 933 and a metal reservoir base 941. The reservoir body 933 includes an externally threaded surface 936 of a sidewall 937 bounding a reservoir cavity 938, and a mounting post 932 is affixed to the reservoir body 933. An ionizer tube 945 defines a passage 946, with a distal end of the ionizer tube 945 connected to a heated ionizer section 951, and with a proximal section 945A of the ionizer tube 945 extending through the reservoir base 941. The proximal section 945A of the ionizer tube 945 in combination with the sidewall 944 of the reservoir base 941 bound an annular recess 948 that is arranged to be exposed to the reservoir cavity 938 defined in the reservoir body 933. A sealing nut 970 includes a medial portion 971 and includes an internally threaded surface 977 arranged to engage the externally threaded surface 936. The graphite tube gasket 910 is arranged within the interior of the reservoir body 933 and the reservoir base 941 proximate to the sidewalls 937, 944. In certain embodiments, the graphite tube gasket 910 has a dual-tapered exterior surface (e.g., with taper angles preferably in a range of 1-5 degrees, or more preferably in a range of 2-3 degrees), with a reduced outer diameter proximate to ends of the gasket 910, and with an increased outer diameter at a position intermediate between the two ends. FIG. 24B is a schematic cross-sectional illustration of a variable diameter graphite tube gasket 910, depicting a maximum outer diameter at an intermediate point and a minimum outer diameter along two ends 911, 912, with exaggerated diametric variation for clarity. The tube gasket 910 includes first and second tapered surfaces 915, 916. The dual-tapered exterior surface of the graphite tube gasket 910 is sized to provide an interference fit, so that only a portion of each tapered surface 915, 916 is easily insertable into the respective reservoir base 941 or reservoir body 933, but then must be forced fully in, thereby allowing the metal reservoir base 941 and reservoir body 933 to cut into the tapered surfaces 915, 916 of the graphite tube gasket and effect a seal. In certain embodiments, the graphite tube gasket includes a constant inner diameter defining an internal recess 918 (as shown in FIG. 24B). In certain embodiments the graphite tube gasket includes a constant inner diameter defining an internal recess 918 (as shown in FIG. 24B).

FIG. 24C is a cross-sectional schematic illustration of portions of the primary ion source of FIG. 24A during an assembly step. During assembly, in certain embodiments the graphite tube gasket 910 is first forced into the reservoir body 933 using a cylindrical Teflon stub 990 that fits loosely into the reservoir cap 937 and is forced against the end of the graphite tube gasket 910 using an extra-long temporary sealing nut 980 that threads onto the externally threaded surface 936, thereby pressing a portion of the graphite tube gasket 910 into the interior of the reservoir base 941. The reservoir body 933 is then put aside and the Teflon stub 990 is removed. After assembling and mounting the ionizer section 951 to the ionizer tube 945, the reservoir body 933 with the graphite tube gasket 910 inserted therein is loaded with dried, degassed cesium carbonate. Thereafter, the reservoir body 933 is forced onto the protruding portion of the graphite tube gasket 910, again using the extra-long temporary sealing nut 980. Once the graphite tube gasket 910 has been forced far enough into the annular recess 948 of the reservoir base 941, the extra-long sealing nut is removed and replaced with the final sealing nut 970 and the assembly is tightened until the graphite tube gasket 910 bottoms out at both ends 911, 912 to yield the assembly of FIG. 24A. Due to the slightly tapered surfaces 915, 916 of the graphite tube gasket 910, and the soft lubricant nature of the graphite, only a small amount of force is required to effect a seal. Preferably, hand-tightening with two small wrenches about 4" long is sufficient. The graphite tube gasket 910 is disposable, together with a graphite capillary insert of the ionizer section 951, but the remaining metal parts of the ion source of FIG. 24A may be re-used.

Upon reading the following description in light of the accompanying drawing figures, those skilled in the art will understand the concepts of the disclosure and will recognize applications of these concepts not particularly addressed herein. Those skilled in the art will recognize improvements and modifications to the preferred embodiments of the present disclosure. All such improvements and modifications are considered within the scope of the concepts disclosed herein and the claims that follow.

What is claimed is:

1. A primary ion source arranged for use with a secondary ion mass spectrometer, the primary ion source comprising:
an ionizer tube defining an internal passage and configured to receive cesium-containing vapor from a reservoir, and
a distal end portion comprising an outwardly protruding conical or frustoconical surface, wherein an ionizer aperture extends through a central axis of the conical or frustoconical surface, and the ionizer aperture is arranged to receive cesium-containing vapor from the internal passage of the ionizer tube;
further comprising one of the following features (a) or (b):
(a) the primary ion source comprises a capillary insert and a cap configured to be positioned at a first end of the ionizer tube, the capillary insert includes a body comprising graphite or a graphite-containing material that defines the ionizer aperture and the conical or frustoconical surface, at least a portion of the capillary insert is configured to be received by the internal passage of the ionizer tube along the first end of the ionizer tube, the cap defines a cavity arranged to receive a portion of the capillary insert and defines an orifice registered with the ionizer aperture, and the cap includes an internally threaded surface configured to engage an externally threaded surface of the ionizer tube to cause sealing engagement between the capillary insert and the ionizer tube; or (b) the primary ion source comprises a reservoir base, wherein the ionizer tube, the reservoir base, and the conical or frustoconical surface are unitary and formed of a continuous graphite or graphite-containing body material.

2. The primary ion source of claim 1, comprising feature (a).

3. The primary ion source of claim 2, wherein the capillary insert comprises a shoulder arranged to abut the first end of the ionizer tube.

4. The primary ion source of claim 3, wherein the at least a portion of the capillary insert configured to be received by the internal passage of the ionizer tube comprises a cylindrical portion arranged proximate to the shoulder and extending into the internal passage of the ionizer tube.

5. The primary ion source of claim 2, wherein the capillary insert further includes a wide channel portion arranged between the ionizer aperture and the internal passage of the ionizer tube.

6. The primary ion source of claim 2, further comprising:
a reservoir base;
a reservoir body;
a tubular gasket arranged between the reservoir base and the reservoir body, wherein the tubular gasket comprises graphite or a graphite-containing body material, the tubular gasket comprises a first end and a second end, and the tubular gasket comprises an outer diameter that varies with position from a maximum diameter value at an intermediate point to reduced diameter values at the first end and the second end; and
a sealing nut comprising internal threads arranged to engage an externally threaded surface of at least one of the reservoir base or the reservoir body;
wherein the ionizer tube is arranged in fluid communication with a reservoir cavity bounded by a portion of the reservoir base, a portion of the reservoir body, and an interior surface of the tubular gasket.

7. The primary ion source of claim 1, comprising feature (b).

8. The primary ion source of claim 7, wherein a portion of the reservoir base is configured to bound a cylindrical cavity of a cavity-defining reservoir body.

9. The primary ion source of claim 8, wherein the reservoir base and a first portion of the ionizer tube in combination define an annular recess arranged to be exposed to the cylindrical cavity of the cavity-defining reservoir body, and a second portion of the ionizer tube extends outwardly from the reservoir base.

10. The primary ion source of claim 9, wherein the ionizer aperture has a reduced diameter in comparison to a nominal or average diameter of the internal passage of the ionizer tube.

11. The primary ion source of claim 8, wherein the reservoir base comprises a tapered graphite cylinder with an outer diameter that varies with position from a maximum diameter value greater than an inner diameter of the cavity-defining reservoir body at an end closest to the ionizer aperture to a reduced diameter value smaller than the inner diameter of the cavity-defining reservoir body at an end furthest from the ionizer aperture, and a sealing cap arranged to threadedly engage a portion of the cavity-defining reservoir body and to force the tapered graphite cylinder into the cavity-defining reservoir body.

12. The primary ion source of claim 1, wherein the conical or frustoconical surface comprises a complementary conical half-angle in a range of from 6 to 45 degrees.

13. The primary ion source of claim 1, wherein the ionizer aperture comprises a diameter of no greater than about 125 μm.

14. A secondary ion mass spectrometer including the primary ion source of claim 1.

15. A primary ion source arranged for use with a secondary ion mass spectrometer, the primary ion source comprising:
a reservoir base;
a reservoir body;
a tubular gasket arranged between the reservoir base and the reservoir body, wherein the tubular gasket comprises graphite or a graphite-containing body material, the tubular gasket comprises a first end and a second end, and the tubular gasket comprises an outer diameter that varies with position from a maximum diameter value at an intermediate point to reduced diameter values at the first end and the second end;
an ionizer tube arranged in fluid communication with a reservoir cavity bounded by a portion of the reservoir base, a portion of the reservoir body, and an interior surface of the tubular gasket; and
a sealing nut comprising internal threads arranged to engage an externally threaded surface of at least one of the reservoir base or the reservoir body.

16. The primary ion source of claim 15, wherein the ionizer tube and the reservoir base are unitary and formed of a continuous graphite or graphite-containing body material.

17. The primary ion source of claim 15, wherein the ionizer tube comprises a proximal end proximate to the reservoir body, and the ionizer tube comprises a distal end defining an ionizer aperture having a reduced diameter in comparison to a nominal or average diameter of a passage within the ionizer tube.

18. The primary ion source of claim 17, wherein the distal end of the ionizer tube comprises an outwardly protruding conical or frustoconical surface, and wherein the ionizer aperture extends through a central axis of the conical or frustoconical surface.

19. The primary ion source of claim 15, further comprising:
a capillary insert including a body defining an ionizer aperture, wherein at least a portion of the capillary insert is configured to be received by the ionizer tube; and
a cap defining an orifice registered with the ionizer aperture, including a cavity arranged to receive a portion of the capillary insert, and including an internally threaded surface arranged to engage an externally threaded surface of the ionizer tube to cause sealing engagement between the capillary insert and the ionizer tube.

20. The primary ion source of claim 19, wherein the capillary insert comprises graphite or a graphite-containing material.

21. The primary ion source of claim 19, wherein the body of the capillary insert comprises a distal end arranged to extend through the orifice defined in the cap, the distal end comprises an outwardly protruding conical or frustoconical surface, and the ionizer aperture extends through a central axis of the conical or frustoconical surface.

* * * * *

UNITED STATES PATENT AND TRADEMARK OFFICE
CERTIFICATE OF CORRECTION

PATENT NO. : 9,941,089 B2
APPLICATION NO. : 15/517917
DATED : April 10, 2018
INVENTOR(S) : Peter Williams et al.

Page 1 of 1

It is certified that error appears in the above-identified patent and that said Letters Patent is hereby corrected as shown below:

In the Specification

In Column 2, Line 46, replace "FIG. 10" with --FIG. 1C--.

In Column 2, Lines 61-62, replace "FIG. 10" with --FIG. 1C--.

In Column 3, Lines 2-3, replace "FIG. 10" with --FIG. 1C--.

In Column 8, Line 22, replace "FIG. 10" with --FIG. 1C--.

Signed and Sealed this
Nineteenth Day of June, 2018

Andrei Iancu
*Director of the United States Patent and Trademark Office*